(12) United States Patent
Blumentritt et al.

(10) Patent No.: US 8,813,584 B2
(45) Date of Patent: Aug. 26, 2014

(54) SYRINGE, SYRINGE FAMILY AND METERING DEVICE

(75) Inventors: Michael Blumentritt, Hamburg (DE); Juergen Loehn, Klein Meckelsen (DE)

(73) Assignee: Eppendorf AG, Hamburg (DE)

( * ) Notice: Subject to any disclaimer, the term of this patent is extended or adjusted under 35 U.S.C. 154(b) by 46 days.

(21) Appl. No.: 12/843,462

(22) Filed: Jul. 26, 2010

(65) Prior Publication Data

US 2011/0088493 A1 Apr. 21, 2011

Related U.S. Application Data

(60) Provisional application No. 61/228,744, filed on Jul. 27, 2009.

(51) Int. Cl.
 *G01N 1/14* (2006.01)
 *B01L 3/02* (2006.01)
 *G01N 35/10* (2006.01)

(52) U.S. Cl.
 CPC .......... *B01L 3/0234* (2013.01); *B01L 2200/14* (2013.01); *B01L 2200/025* (2013.01); *G01N 2035/103* (2013.01); *B01L 2300/0858* (2013.01); *B01L 2200/0689* (2013.01); *B01L 2200/0605* (2013.01); *B01L 2400/086* (2013.01); *B01L 2200/0684* (2013.01); *B01L 3/0217* (2013.01)
 USPC ..................................................... 73/864.13

(58) Field of Classification Search
 None
 See application file for complete search history.

(56) References Cited

U.S. PATENT DOCUMENTS

| | | | | |
|---|---|---|---|---|
| 2,660,342 A | * | 11/1953 | Herman Ruf | .................. 222/340 |
| 4,082,121 A | * | 4/1978 | Sturm et al. | ..................... 141/27 |
| 4,406,170 A | | 9/1983 | Kuhn | |
| 4,750,373 A | * | 6/1988 | Shapiro | ..................... 73/864.87 |
| 5,620,660 A | | 4/1997 | Belgardt et al. | |
| 6,455,006 B1 | * | 9/2002 | Mukai | ........................... 422/501 |
| 7,754,494 B1 | * | 7/2010 | Verkaart et al. | ............... 436/180 |
| 2006/0263261 A1 | | 11/2006 | Lenz | |
| 2009/0139351 A1 | * | 6/2009 | Reichmuth et al. | ........ 73/864.11 |
| 2010/0266454 A1 | * | 10/2010 | Reichmuth | .................... 422/100 |
| 2011/0072915 A1 | * | 3/2011 | Molitor et al. | ............. 73/864.11 |

FOREIGN PATENT DOCUMENTS

| | | |
|---|---|---|
| DE | 27 36 551 A1 | 3/1978 |
| DE | 2926691 A1 | 6/1981 |
| DE | 4341229 A1 | 6/1995 |
| DE | 102004063652 A1 | 7/2006 |
| DE | 102005023203 A1 | 11/2006 |
| DE | 69836896 T2 | 11/2007 |
| EP | 0657216 A2 | 10/1994 |

\* cited by examiner

*Primary Examiner* — Robert R Raevis
(74) *Attorney, Agent, or Firm* — Vidas, Arrett & Steinkraus, P.A.

(57) ABSTRACT

Syringe for use with a metering device comprising a centering element with an axial through-passage in a receiver for a syringe cylinder and an axially displaceable piston receiver for a syringe piston, comprising
 syringe cylinder
 syringe piston,
 the syringe cylinder comprising an outlet at the bottom,
 centering flange at the top on the external periphery for inserting into the receiver,
 cylindrical piston movement area connected to the outlet, with a first internal diameter, in which the syringe piston is sealingly guided, and
 at least at a distance of at least 3 mm from the upper end of the syringe cylinder a centering region for inserting the centering element, which has a second internal diameter, which exceeds the first internal diameter and is at least 16.2 mm,
 the syringe piston at the upper end has a coupling piece for inserting into the piston receiver.

13 Claims, 19 Drawing Sheets

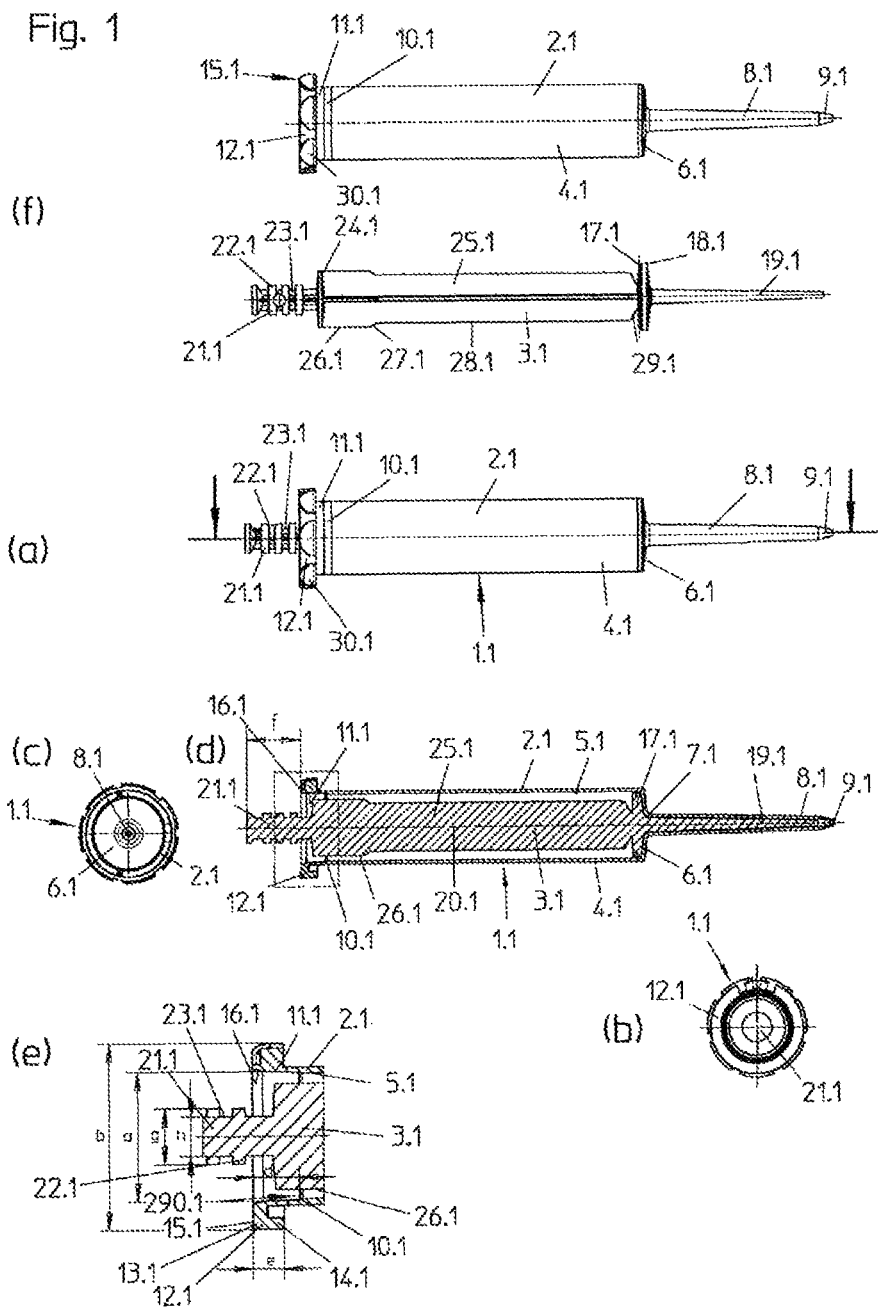

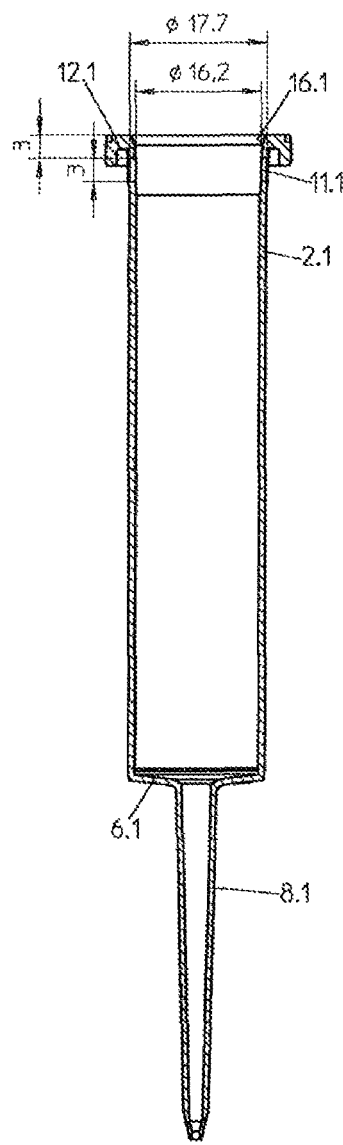

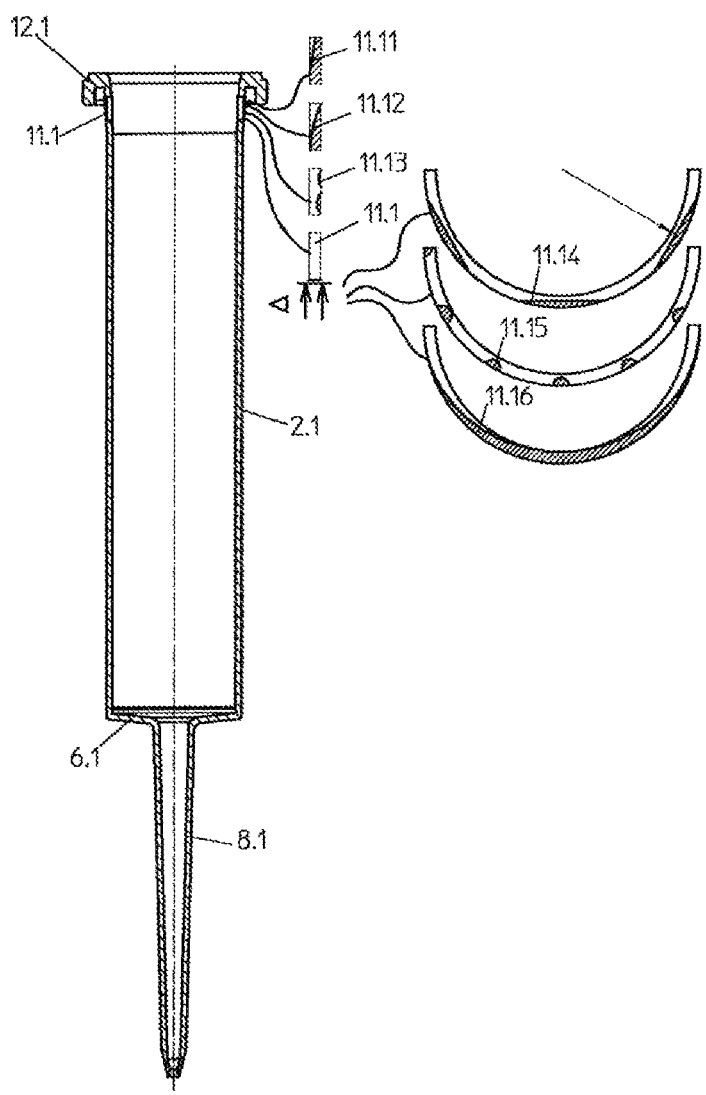

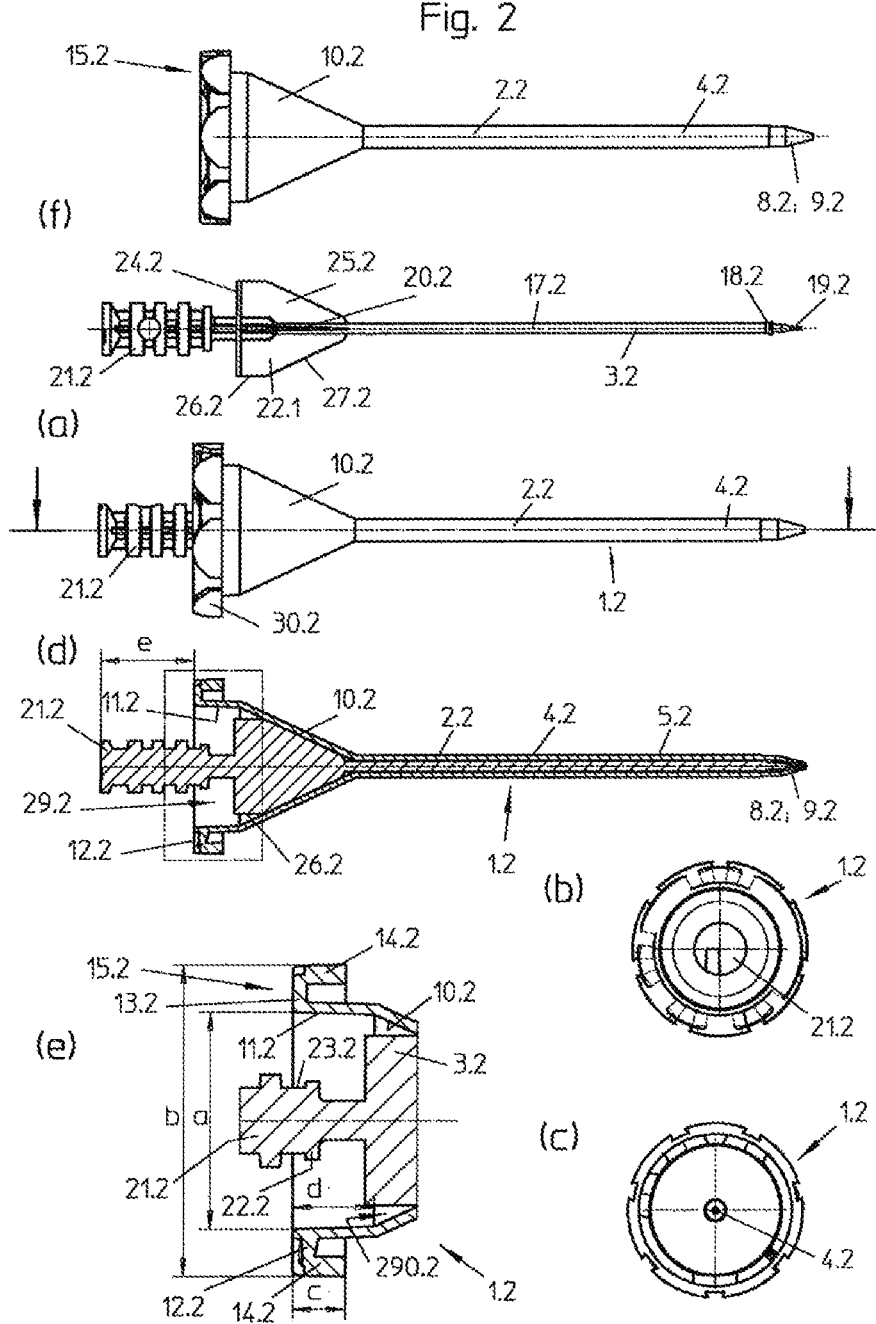

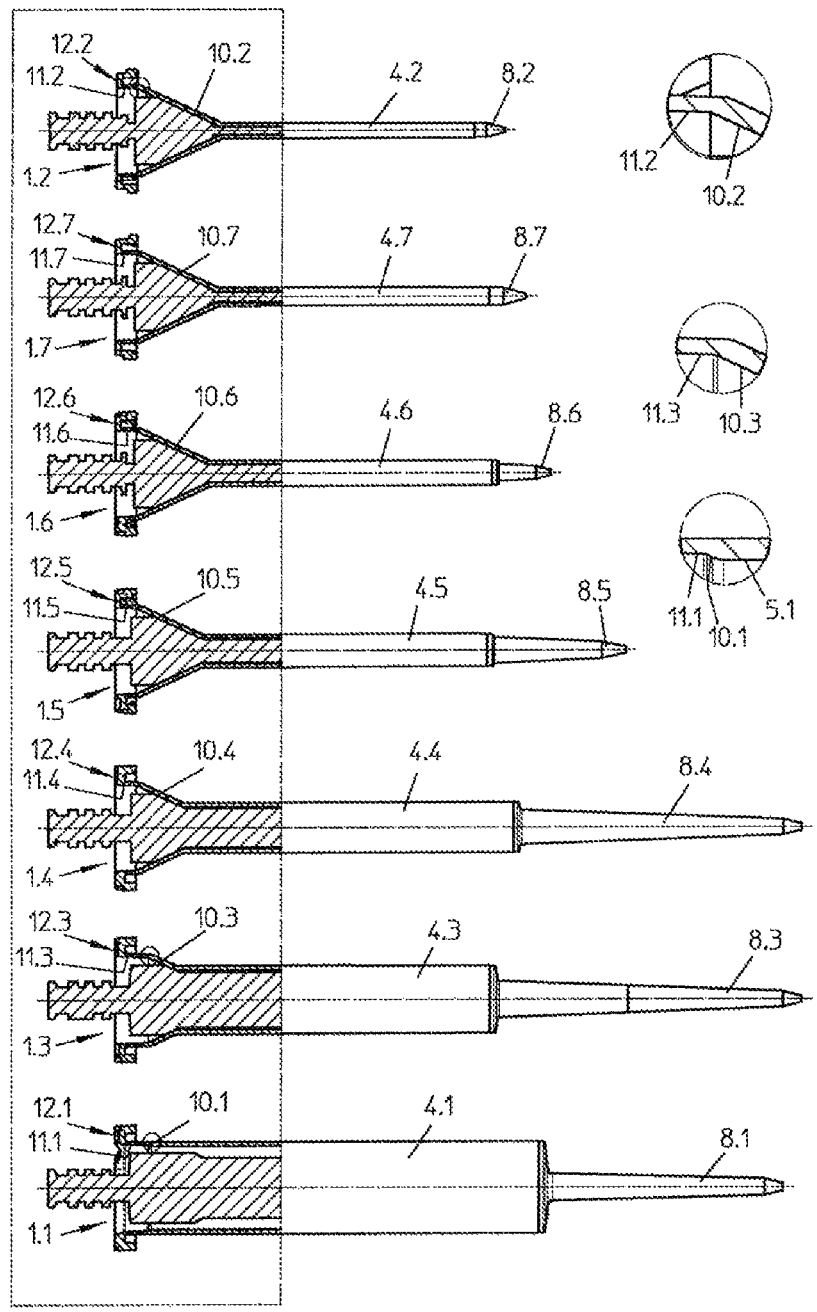

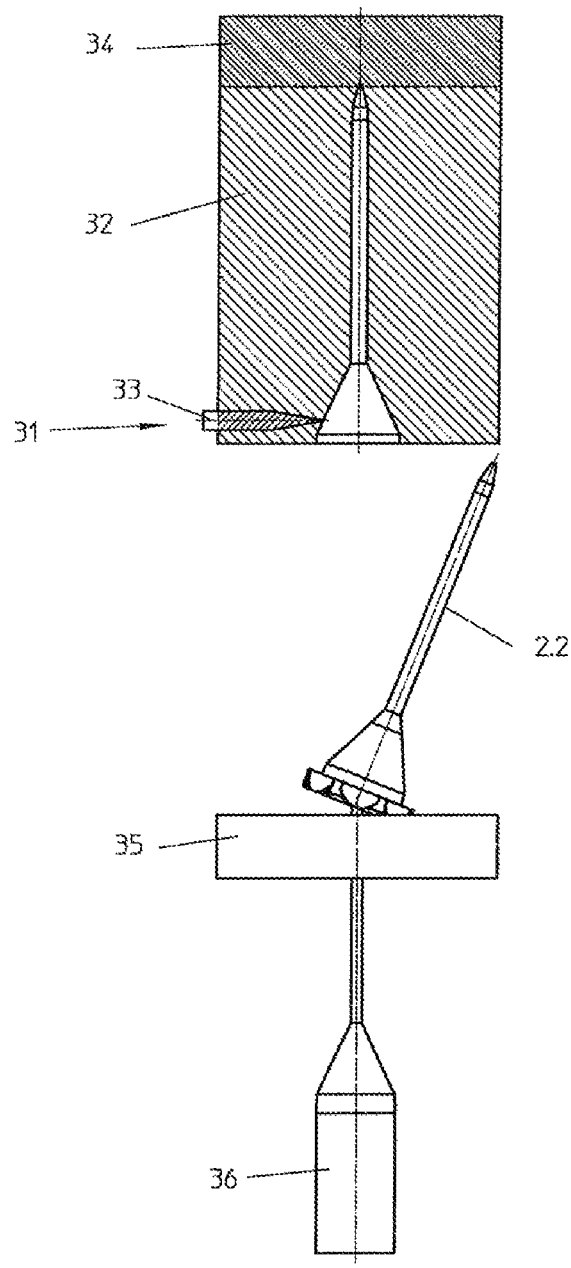

Results

| Nr | Fmax N | e-F max mm |
|---|---|---|
| 1 | 1.74 | 1.96 |
| 2 | 1.79 | 1.97 |
| 3 | 3.09 | 1.98 |
| 4 | 3.18 | 1.97 |
| 5 | 2.46 | 1.97 |
| 6 | 2.40 | 1.97 |

SYRINGE, SYRINGE FAMILY AND METERING DEVICE

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention relates to a syringe and a syringe family for use with a metering device and to a metering device for use with a syringe or a syringe family.

Pipettes are metering devices for measuring out and transferring liquids. They are frequently designed as repeater pipette or multipipettes, which are used together with a syringe, in order to draw liquid into the syringe and gradually to discharge said liquid therefrom. A repeater pipette is known from DE 29 26 691 C2, the entire contents of which is incorporated herein by reference, and U.S. Pat. No. 4,406,170, the entire contents of which is incorporated herein by reference, which, in particular, discloses the repeating mechanism of the repeater pipette. It also discloses the fixing of the syringe to the repeater pipette. To this end, the syringe has a syringe flange which may be inserted from the side into a substantially U-shaped groove of the pipette, which is open at the side. An axial pressure spring secures the inserted syringe flange in the groove. For connecting the syringe piston to a piston adjusting device of the pipette, an insertion element is present which receives an end portion of the syringe piston between two jaws. The jaws are able to be pressed against the syringe piston by means of a flap-shaped clamping member, the actuating lever thereof protruding from the housing through an opening. This manner of fixing the syringe has the drawback that the syringe has to be handled for insertion and coupling to the piston adjusting device and/or for uncoupling and removal.

DE 43 41 229 C2, the entire contents of which is incorporated herein by reference, and U.S. Pat. No. 5,620,660, the entire contents of which is incorporated herein by reference, propose a pipette system which is more suitable for manual actuation with a syringe which may simply be inserted axially into the pipette and/or may be removed therefrom. This pipette system has a syringe comprising a fastening portion and a syringe piston, and a pipette which comprises in a pipette housing a receiver for the fastening portion and a receiving body with a piston receiver for the syringe piston and/or a piston rod connected thereto. In addition, fastening devices are present for the reversible and/or releasable fixing of the fastening portion and syringe piston in the receivers and piston adjusting devices are present for displacing the receiving body in the pipette housing. The fastening portion and the syringe piston are able to be pushed into their fastening positions through axial openings in their receivers.

The fastening devices have gripping devices which may be positioned radially for fixing the fastening portion and the syringe piston in the fastening positions. The gripping devices have syringe gripping levers mounted pivotably in the pipette housing and piston gripping levers mounted pivotably in the receiving body. The syringe gripping levers and the piston gripping levers are designed to be double-armed with a gripping arm and an actuating arm, the syringe gripping levers comprising contact points on the inner faces of their actuating arms, which by the actuation of their actuating arms are able to be pivoted externally against the actuating arms of the piston gripping levers and actuate the piston gripping levers.

As a result, it is achieved that the syringe and the pipette are able to be connected to one another by a purely axial relative movement and are able to be separated from one another by actuating the actuating arms. According to one embodiment, the fastening portion is a syringe flange and according to a further embodiment the syringe piston has a piston flange for engaging behind the gripping devices.

From DE 10 2005 023 203, the entire contents of which is incorporated herein by reference, and US 2006263261 A1, the entire contents of which is incorporated herein by reference, an embodiment of the pipette according to DE 43 41 229 C2, the entire contents of which is incorporated herein by reference, is known in which the syringe may be released from the pipette by the actuation of just one actuator.

The commercial Multipette® (plus/stream/X-stream) embodiments of this metering system from Eppendorf AG comprise Combitips® (plus) syringes, which have a cylinder with a piston movement area on the inside and a syringe flange at the upper end of the cylinder. The syringes are supplied with various filling volumes (0.1 ml, 0.2 ml, 0.5 ml, 1 ml, 2.5 ml, 5 ml and 10 ml). The internal diameter of the piston movement area is dimensioned so that the filling volume is received into the syringe and/or discharged therefrom with a maximum piston adjusting path of the Multipette® of Eppendorf AG of 50 mm plus an over-stroke of a few millimeters. In the syringe with a nominal volume of 10 ml accordingly the internal diameter of the piston movement area is 15.96 mm With smaller syringes, the internal diameter of the piston movement area is correspondingly smaller. The cylinders of the smaller syringes have at the upper end of the piston movement area a cylindrical widening, the internal diameter thereof being in each case markedly smaller than 15.96 mm and which is all the smaller, the smaller the filling volume of the syringe. One reason for the cylindrical widening is that, as a result, a depth stop of the piston may be produced in the cylinder, whereby damage to the piston sealing lip is prevented from occurring by positioning the sealing lip on the lower front face of the cylinder. A further reason is that in the small syringes, the piston area below the coupling piece inserted into the metering system is designed to be thicker, in particular is designed as a wing piece, in order to achieve as a result an increase in the resistance to buckling of the piston rod in the stored state.

Proceeding from the flange, the cylinders have on the periphery four axially extended ribs protruding outwardly, which are distributed uniformly over the periphery. The ribs have at the bottom one respective shoulder for supporting on the edge of holes of a tray or a box. So that syringes of different filling volumes may be inserted into uniform holes of a tray or a box, the shoulders of syringes which have different filling volumes are the same distance from the axis of the cylinder.

The known metering system permits accurate metering with low measurement deviation.

Proceeding therefrom, the object of the invention is to provide a syringe and a syringe family for use with a metering device and a metering device for use with a syringe or a syringe family which permit even more accurate metering.

The object is achieved by a syringe having the features of Claim 1.

A syringe according to the invention for use with a metering device comprising a centering element with an axial through-passage in a receiver for a syringe cylinder and an axially displaceable piston receiver for a syringe piston has
a syringe cylinder
and a syringe piston,
the syringe cylinder comprising an outlet at the bottom,
a centering flange at the top on the external periphery for inserting into the receiver,
a cylindrical piston movement area connected to the outlet, with a first internal diameter, in which the syringe piston is sealingly guided, and
at least at a distance of at least 3 mm from the upper end of the syringe cylinder a centering region for inserting the centering element, which has a second internal diameter which exceeds the first internal diameter and is at least 16.2 mm and at most 17.7 mm,
and the syringe piston at the upper end has a coupling piece for inserting into the piston receiver.

The syringe family according to the invention for use with a metering device comprising a centering element with an axial through-passage in a receiver for a syringe cylinder and an axially displaceable piston receiver for a syringe piston comprises
a plurality of syringes with different filling volumes, in each case comprising
a syringe cylinder
and a syringe piston,
the syringe cylinder comprising an outlet at the bottom,
a centering flange at the top on the external periphery for inserting into the receiver,
a cylindrical piston movement area connected to the outlet in which the syringe piston is sealingly guided, and
at least at a distance of at least 3 mm from the upper end of the syringe cylinder a centering region for inserting the centering element,
the syringe piston at the upper end comprising a coupling piece for inserting into the piston receiver
and the centering regions of the syringes with different filling volumes having a matching contour on the inside.

The plurality of syringes are preferably selected from the group of syringes which have filling volumes of 10 ml, 5 ml, 2.5 ml, 1 ml, 0.5 ml, 0.2 ml and 0.1 ml.

The centering regions of the syringes which have different filling volumes have a matching contour. By "matching contour" in the centering region is understood the same and/or different geometries, which are tailored to the same predetermined centering contour. The syringes which have a matching contour are, therefore, suitable for cooperating with one and the same centering element of the metering system which has the centering contour.

The metering device according to the invention for use with a syringe comprising a syringe cylinder and a syringe piston, the syringe cylinder comprising an outlet at the bottom, a centering flange at the top on the external periphery, a cylindrical piston movement area connected to the outlet, in which the syringe piston is sealingly guided, and further above a centering region and a coupling piece at the upper end of the syringe piston or for use with a syringe family comprising a plurality of such syringes, has
a housing comprising
a receiver for the centering flange of the syringe cylinder with an axial opening for axially inserting the centering flange into a fastening position,
a centering element arranged in the receiver, aligned with the axial opening, with an axial through-passage for axially inserting the syringe cylinder into the centering region,
a receiving body with a piston receiver for axially inserting the coupling piece into a fastening position,
fastening devices for releasably holding the centering flange and coupling piece in their fastening positions in the receiver and in the piston receiver,
the fastening devices comprising radially positionable gripping devices for gripping the centering flange and the coupling piece in the fastening positions,
and piston adjusting devices for displacing the receiving body in the housing.

The terms "at the top" and "at the bottom" refer to the preferred alignment of the syringe when metering, in which the syringe is held vertically with the outlet at the bottom and the centering flange at the top.

The metering device may, in particular, be a manipulable and/or stationary metering device, driven manually and/or by motor. It may, in particular, be a pipette, a repeater pipette, dispenser, metering station or automatic metering device. Preferably, it is a dispenser.

The syringe according to the invention is able to be fixed easily to a metering device according to the invention in a reversible manner To this end, the syringe is inserted in the axial direction into the metering device, the centering flange being gripped by means of radially positionable gripping devices for gripping the centering flange in the receiver of the metering device and the syringe piston being gripped on its coupling piece in the piston receiver by radially positionable gripping devices for gripping the piston rod. The gripping of the centering flange and of the coupling piece by the gripping devices may be controlled by the axial insertion of the syringe in the receiver of the metering device. To this end, the metering device may be designed as disclosed in DE 43 41 229 C2, the entire contents of which is incorporated herein by reference, and U.S. Pat. No. 5,620,660, the entire contents of which is incorporated herein by reference. The embodiments relative thereto of the aforementioned patents are incorporated in the present application.

When inserting the syringe into the metering device the centering element axially penetrates the centering region and bears radially against the inside of the centering region. The dimensions and geometries of the centering element and of the centering region are tailored to one another, so that the syringe cylinder is centred by the inserted centering element. As a result, the syringe cylinder with the centering region is guided accurately into the receiver so that it may be gripped easily and securely by the gripping devices.

By the bearing of the centering region on the centering element, a deformation in the centering region of the syringe cylinder may be corrected. In particular, the centering element may correct a non-circular shape of the syringe cylinder to form an ideal circular shape. As the centering region is either located in the immediate vicinity of the piston movement area, which is crucial for accurate metering, or in the immediate vicinity of the transition region, which counteracts damage to the sealing lip of the piston, the correction in the centering region acts positively on the metering accuracy. A non-circular cylinder has a cross-sectional area which is different from the circular cylinder, which leads to metering errors. In particular, by the circular shape the tightness of the seal of the syringe piston in the cylinder and thus the accuracy of the metering is improved. A non-circular syringe cylinder, due to the altered cross-sectional area, also has the result that, in particular, at the end of the receiving stroke and during the initial discharge strokes air flows past the syringe piston and a small volume of liquid is received and/or discharged. This drawback is overcome by the invention.

In addition, the guidance of the centering region on the centering element prevents faulty alignment of the syringe relative to the metering device and tilting of the syringe relative to the metering device under load. A faulty alignment may occur with a conventional metering system, when the syringe is gripped in tilted alignment by the gripping devices of the metering system. Tilting under load may occur with a conventional metering system if, during metering, the syringe in the vicinity of its outlet touches a wall with a contact force. This type of discharge is denoted as wall discharge. In particular, it is used with small discharge volumes in order to avoid errors by uneven drop break from the syringe. As a result, the syringe cylinder is pivoted relative to the syringe piston, whereby liquid is displaced and a metering error may result. Additionally, reduced tightness of the seal of the piston in the tilted syringe cylinder may impair the accuracy of the metering. These disadvantageous features of the previously known syringe and metering devices are also overcome by the present invention.

For centering the syringe, it is important that the centering element bears against the centering region at a distance from the upper end of the syringe cylinder. Only when the centering element engages correspondingly deeply in the syringe piston, is it able to bear all around the centering region and correct a non-circular shape of the syringe cylinder, align and support it and thus prevent tilting. The stiffening of the syringe cylinder by the centering flange at the upper end of the syringe works against the correction of a non-circular cross section in the piston movement area. Thus the second internal diameter of at least 16.2 mm of the centering region of the syringe according to the invention and/or the centering region of the syringes of the syringe family according to the invention is present at least at a distance of at least 3 mm from the upper end of the syringe cylinder, i.e. in the immediate vicinity of the piston movement area and/or the transition region. The centering region is thus also characterized by its immediate vicinity to the piston movement area.

The syringe piston may be inserted with its coupling piece through the axial through-passage of the centering element, so that the syringe piston may be pulled out of the syringe cylinder. Optionally, the piston receiver engages in the axial through-passage of the centering element for coupling the coupling piece.

The internal diameter in the centering region of at least 16.2 mm ensures that syringes with a filling volume of up to 10 ml with an internal diameter of the piston movement area of up to 15.96 mm may be inserted into a metering device with a maximum piston adjusting path of 50 mm, plus an over-stroke of a few millimeters. Thus syringes of all current filling volumes are covered by the invention. Larger filling volumes (for example 25-50 ml) are possible when an adapter is used, which reduces the larger diameter of the syringe cylinder to the smaller diameter of the receiver of the metering device. An adapter is useful, even with small-volumed syringes, as it facilitates the ability of small syringes to be grasped and handled. Preferably, the adapter has the centering region. As a result, the adapter is also centred in the metering device and thus aligns the syringe, supports it and prevents tilting of the syringe, in particular during wall discharge.

The invention includes syringes in which the syringe cylinder is in one piece. In addition, the invention includes syringes in which the syringe cylinder is in several parts. In particular, the invention includes syringes in which the syringe cylinder has the piston movement area and the outlet on a lower part and the centering flange and the centering region on an upper part, which may be connected to the lower part, for example by means of a bayonet, screw and/or snap connection. The upper part may, in particular, be an adapter.

The internal diameter of the centering region of the syringe according to the invention exceeds the internal diameter of the piston movement area, so that during injection-moulding the syringe cylinder may be filled more evenly with plastics material and thus made more dimensionally stable. The step change of the internal diameter between the piston movement area and the centering region namely produces a flow brake, which preferably forces the hot plastics mass injected below the centering region to fill initially the lower part of the syringe cylinder and thus the piston movement area uniformly and subsequently the centering region and the centering flange. As a result, the dimensional stability of the syringe cylinder in the piston movement area and thus the accuracy of the metering are improved.

Moreover, a step change in the internal diameter between the piston movement area and the centering region makes it possible for the syringe piston which is fully inserted into the syringe cylinder to be guided at the top in the piston movement area, when the syringe is not connected to the metering device. To this end, the external diameter of a guide region of the syringe piston arranged below the coupling piece may approximately correspond to the internal diameter of the piston movement area. The external diameter of the guide region should be less than the internal diameter of the piston movement area by at least the sum of the tolerances of the syringe piston (for example 0.1 mm) and the syringe cylinder (for example 0.1 mm). Due to the larger internal diameter in the centering region, a gap remains between the syringe piston and the centering region, into which the centering element may be inserted. Thus by the widening of the internal diameter in the centering region relative to the internal diameter in the piston movement area a centering of the syringe piston in the syringe is ensured, when the syringe is connected to the metering device and the centering element engages in the widened centering region and fills said region. The centering and guiding of the syringe piston in the syringe separated from the metering device is provided in spite of the widened centering region, as the guide region of the fully inserted syringe piston bears against the piston movement area and is guided, and/or in syringes with small volumes (for example 1 ml and below) against the transition region.

The centering of the syringe piston by the guide region in the syringe separated from the metering device avoids tilting of the syringe piston in the syringe cylinder and thus deformation in the sealing region of the syringe piston and/or the syringe cylinder by partial irreversible widening, whereby metering errors are avoided.

The guiding of the syringe piston at the top in the piston movement area may be effected by wings of the syringe piston protruding outwardly and extending axially and/or by a disc below the coupling piece of the syringe piston. The disc may additionally effect a covering of the piston movement area, which prevents penetration of dirt into the syringe cylinder, which may impair the seal of the piston and/or may contaminate the liquid to be metered.

In addition, the step change in the internal diameter between the centering region and the piston movement area permits tolerances to be monitored in a simple manner by means of force measurement when the syringe piston and the syringe cylinder are joined together during manufacture. If the diameter of the syringe piston is too large, two force increases are measured during the joining process, namely when the syringe piston penetrates the centering region with its sealing region and then when the sealing region penetrates the piston movement area. If the diameter of the piston does not exceed the tolerance upper limit, a force increase is only measured when the sealing region penetrates the piston movement area. By simple and clear measurement, it may thus be established whether the diameter of the syringe piston exceeds the tolerance upper limit and the syringe piston has to be discarded. It is particularly important to monitor that the tolerance upper limit has been maintained, as non-circularity of the syringe piston may be established as an enlargement of the diameter. The use of syringe pistons which, due to a non-circular sealing region, cause metering errors, may thus be avoided. As the tolerances of the syringe piston and the syringe cylinder are tested, when the tolerance upper limit is exceeded preferably the entire syringe is discarded. The present invention, therefore, also comprises a method for testing the tolerances.

BRIEF SUMMARY OF THE INVENTION

According to the inventive method for testing the tolerances of syringes with a cylindrical piston movement area with a first internal diameter and a centering region with a second internal diameter, which exceeds the first internal diameter, when inserting a syringe piston into the syringe cylinder the force for inserting the syringe piston into the syringe cylinder is measured and in the event that the force for inserting the syringe piston into the centering region exceeds a tolerance upper limit, the syringe piston and/or the syringe cylinder is discarded.

After use, the syringe may be easily released from the metering system by actuating the gripping devices. The removal may also be carried out in an axial movement. As a result of the centering, jamming of the syringe cylinder in the receiver is avoided so that the removal may be carried out more easily. In particular, after releasing the gripping devices the syringe may fall out of the metering system due to its own weight. This may optionally be assisted by a resilient stop, to which the centering flange of the syringe cylinder may be fixed.

The internal diameter in the centering region of the syringe according to the invention is at most 17.7 mm. By limiting the internal diameter in the centering region to a maximum value of 17.7 mm it is achieved that the syringes may be gripped by means of a conventional dispenser of the Multipette® type from Eppendorf AG, when they are held in a tray. In these metering systems, the gripping devices have hook-shaped gripping ends for releasably fixing the syringe flange, the internal edges thereof in the pivoted-together state having a spacing of 20.8 mm from one another. The syringes may be provided in a tray with support sleeves protruding from a plate. The syringes may be inserted into holes of the support sleeves, the syringe cylinder being guided on the external periphery of the centering region in the support sleeves. So that the syringe gripping levers are not clamped tightly on the support sleeves, the external diameter of the support sleeves may be selected so that it is less than the distance between the gripping ends pivoted together. Taking into account a minimum wall thickness of the support sleeves, a clearance for inserting the syringe cylinder into the support sleeves and a minimum wall thickness for the syringe cylinder in the centering region, the internal diameter in the centering region is at most 17.7 mm.

The syringe is preferably produced from plastics material, in particular a thermoplastic material. Preferably the thermoplastic material is selected from the polyolefin group. Preferred polyolefins are polyethylene (PE), polypropylene (PP) as well as cyclic olefin (Co)polymers, abbreviated to COC or COP. Syringes and pistons may be produced from one and the same plastics material, or from different plastics materials. In particular, due to the improved friction pairing, the piston is made of PE and the cylinder is made of PP or vice versa.

The syringe according to the invention may be designed so that it may be also be used in conventional dispensers of the Multipette® type from Eppendorf AG which have no centering element.

The advantageous effects of the syringes according to the invention are, in principle, also provided in the syringes of the syringe family according to the invention. In syringes with different filling volumes of the syringe family, the centering regions have contours which are tailored to the same predetermined centering contour, so that they may be used with the same metering device, the centering element thereof comprising the centering contour. In any application, the user is able to use a syringe with a suitable filling volume and the metering accuracy is always improved by the centering of the respective syringe in the metering device.

Preferably, to this end syringes with different filling volumes of the syringe family have the same contours in the centering regions. They may, however, also have at least partially different contours, provided said contours are tailored to one and the same centering contour. For example, cylindrical and polygonal contours may be tailored to the same cylindrical centering element, so that the centering regions provided with these different contours are centred by one and the same centering element. The centering regions of syringes with different filling volumes of a syringe family thus have a functionally matching contour which is tailored to the same predetermined centering contour. By a "matching contour" in the centering region, therefore, is understood the same and/or different contours and/or geometries, which cooperate with the same centering element of a metering device which has the predetermined centering contour, i.e. complementary thereto. In particular, this means that in a syringe family with a plurality of syringes with different filling volumes, between the individual members with different filling volumes (for example 10 ml, 5 ml, 2.5 ml, 1 ml, 0.5 ml, 0.2 ml and 0.1 ml), different contours and/or geometries may be present in the centering region which are nevertheless all characterised in that the same centering element of a metering system engages therein, bears thereagainst and thus corrects possible non-circularity of the syringe cylinder, as well as aligns and supports the syringe.

According to one embodiment of the invention, within a syringe family for an individual member of the family the matching contour and/or geometry in the centering region is selected from the group of conical hollow bodies, convex hollow bodies, pyramidal hollow bodies, columnar hollow bodies with an elliptical outer base and/or cross-sectional area, polygonal columnar, in particular octagonal columnar hollow bodies, hollow bodies with peripheral and/or partially peripheral ribs or projections, hollow bodies with at least two flattened inner faces, and/or hollow bodies which are intersected by at least two secants, hollow bodies with protrusions, studs, projections and elliptical hollow bodies and a combination thereof. Preferred combinations are conical with a peripheral bead, for example as a torus, a combination of conical and cylindrical as well as conical, with projections or circular raised portions.

According to one embodiment of the invention, the predetermined centering contour of the centering element is also selected from the aforementioned groups.

According to a preferred embodiment, the syringes of the syringe family in the centering region have an internal diameter of at least 16.2 mm and at most 17.7 mm.

In principle, the syringe family may have a syringe with a filling volume of 10 ml, which in the piston movement area and in a centering region has the same internal diameter of 15.96 mm. A second internal diameter of at least 16.2 mm is an advantageous embodiment of the syringes of the syringe family according to the invention which ensures that a syringe with a filling volume of 10 ml also has the advantages of a centering region with a larger internal diameter than in the piston movement area.

According to one embodiment, the syringe cylinder in the cylindrical piston movement area has a greater wall thickness than in the centering region. As a result, a particularly effective flow brake is achieved as, for increasing the flow resistance due to the deflection of the flow of the hot plastics mass in the region of the diameter step change, an increase in the flow resistance results, due to the reduced flow cross section.

According to a further embodiment, the syringe cylinder has a conical insertion region at the upper end of the centering region and/or a conical transition region between the centering region and the cylindrical piston movement area. The conical insertion region and/or the conical transition region guide the syringe piston when inserted into the piston movement area, so that the sealing region of the piston is correctly inserted and not damaged. Preferably, the insertion region and/or the transition region are at an angle of 15 to 30° to the axis of the syringe cylinder. Particularly preferably, an angle of the insertion region of approximately 15° and an angle of the transition region of approximately 25° is preferred. In smaller syringes (for example with a filling volume of a maximum of 5 ml) an insertion region may be dispensed with, as the internal diameter in the centering region is sufficiently large for contactless insertion of the syringe piston and said syringe piston may be inserted correctly into the piston movement area, solely through the transition region.

The centering region may be designed in different ways. It may be designed on the inside as a freeform surface or a control surface. By a "freeform surface" is understood a surface which may not be accurately described mathematically, whereas a control surface may be accurately described mathematically. Preferably, it has on the inside the contour and/or geometry of a rotational surface (for example a cylindrical, spherical, hyperbolic, parabolic surface). Preferably, the centering region is slightly conical with a cone angle of 0.5 to 5°, in particular 2° from the longitudinal axis of the syringe. The contour and/or geometry of the centering region may be configured to be smooth on the inside. According to one alternative embodiment of the invention, the centering region has on the inside a contour with projections and/or recesses, the larger imaginary circle inscribed in the contour comprising the second internal diameter. The larger imaginary inscribed circle corresponds to the external diameter of the centering element. The contour and/or geometry of the centering region in cooperation with a complementary centering contour and/or geometry of the centering element leads to a correction of a potentially non-circular shape of the syringe cylinder, and to an alignment and support of the syringe piston and thus prevents a tilting of the piston in the syringe cylinder. Moreover, the cooperation of the contour and/or geometry of the centering region with the complementary centering contour and/or geometry of the centering element permits the correct alignment of a syringe code relative to a sensor for sensing the syringe code and/or anti-twist protection. The anti-twist protection prevents a rotation of the syringe in the metering device, which may damage a sensor for sensing the syringe code. The contour may further serve for reducing the friction between the syringe cylinder and centering element, in order to facilitate the insertion of a smooth centering element in the centering region.

The contour and/or geometry may be tangent to the larger imaginary/projected inscribed circle only on two points which diametrically oppose one another, whereby centering is already achieved. Preferably it is tangent to the circle at more than two points. Preferably, the points are distributed evenly over the circumference of the circle.

The centering element of a metering system, which cooperates with the syringes of the syringe family has an external diameter of 16.2 to 17.7 mm and/or a wall thickness of 0.4 to 2.5 mm and/or projects relative to a stop for the upper face of the centering flange by 2.2 to 6 mm.

According to one embodiment, the centering flange has an external diameter of 21 to 24.2 mm and/or a height of 3.2 to 5.4 mm and/or the centering region is located at least at a distance of a minimum of 3 mm and a maximum of 6 mm from the upper end of the syringe cylinder. This permits an insertion of the syringe into commercial dispensers of the Multipette® type from Eppendorf AG.

According to one embodiment, the syringe has a filling volume selected from the volumes 10 ml, 5 ml, 2.5 ml, 1 ml, 0.5 ml, 0.2 ml, 0.1 ml. The centering region always ensures accurate centering on a centering element of a metering system.

According to one embodiment, the syringe piston has a disc and/or axially extending wings below the coupling piece and between the disc and/or the wings and the centering region an annular gap is present with a gap width of 0.5 to 2.5 mm. The disc prevents a penetration of dirt into the syringe cylinder and the disc and/or the wings guide the syringe cylinder at the top in the piston movement area. By the annular gap with a gap width of 0.5 to 2.5 mm it is ensured that the centering element is arranged between the disc and/or wings and the syringe cylinder and the disc and/or wings may be inserted into the centering element.

The centering element may, in particular, be a torus or hollow cylinder of low height. In addition, it may be configured as a hollow cylinder of greater height, a hollow sphere or as a further continuous rotational body so that a linear contact or surface contact is possible with the centering region. Also, multipoint contact may be expedient. Thus, the centering element may, in particular, be pyramidal or polygonal columnar, the pyramid or the polygonal column being able to have any number of corners (for example 8). Preferably, the centering element is cylindrical, in particular circular cylindrical, or slightly conical, in particular with a cone angle of 0.1 to 2.5°, in particular approximately 1°. Further preferably, the centering element at the lower end has a conical insertion region.

According to a further embodiment, the centering element has on the outside a contour with projections and/or recesses, the smallest circle which the contour circumscribes comprising the second internal diameter. This contour may interlock with a complementary contour of the syringe. As a result, a syringe code may be aligned directly with a sensor of the metering device. In addition, as a result, an anti-twist protection may be effected, which prevents the syringe from twisting in the coding device. In addition, by cooperating with a smooth centering region the contour may reduce the friction when inserting the centering element into the syringe.

According to one embodiment, the centering element is arranged rigidly relative to the receiver or resiliently relative to the receiver in the axial direction. The rigid arrangement produces a more rigid guidance of the syringe relative to the metering device in comparison with the resilient arrangement. The rigid arrangement has the advantage that a resilient stop, against which the centering flange bears with its upper face, assists the release of the syringe from the metering device. An advantage of the rigid arrangement is that it may prevent tilting, when the syringe is positioned with a certain force on a substrate, for example the edge of a receptacle, as for example is usual with the already-discussed pipetting technique of wall discharge. A resilient centering element may compensate for alignment errors when inserting the centering tube into the receiver. According to a preferred embodiment, the centering element is resilient relative to the receiver, by being fixed to a resilient stop for the centering flange.

According to one embodiment, the centering element in the contact region with the centering region has an external diameter of 16.2 to 17.7 mm and/or a wall thickness of 0.4 to 2.5 mm and/or protrudes relative to a stop for the upper face of the centering flange by 2.2 to 6 mm. This information refers to the state of the metering device when the syringe is not inserted, and includes both arrangements of the centering element and stop which are resilient relative to one another and which are also rigid relative to one another. If the stop is configured as a sensor plate, the information refers to the base of the sensor plate, from which optionally contact elements protrude.

The invention is described in more detail hereinafter with reference to the accompanying drawings of exemplary embodiments, in which:

BRIEF DESCRIPTION OF THE SEVERAL VIEWS OF THE DRAWINGS

FIGS. 1a to h show a syringe with a filling volume of 10 ml in side view (FIG. 1a), a view from above (FIG. 1b), a view from below (FIG. 1c), a vertical section along the line A-A of FIG. 1a (FIG. 1d), an enlarged detailed view A of FIG. 1d (FIG. 1e), broken down into the syringe piston and syringe cylinder in side view (FIG. 1f) and a syringe cylinder of the same syringe in a vertical section (FIG. 1g) and the same syringe cylinder in vertical section with variants of the centering region in vertical partial sections and in enlarged half-cross sections (FIG. 1h);

FIGS. 2a to f show a syringe with a filling volume of 0.1 ml in side view (FIG. 2a), a view from above (FIG. 2b), a view from below (FIG. 2c), a vertical section along the line A-A of FIG. 2a (FIG. 2d), enlarged detailed view A of FIG. 2d (FIG. 2e) and broken down into the syringe piston and syringe cylinder in side view (FIG. 2f);

FIGS. 3a and b show syringes of a syringe family in side view with a cutaway portion in the upper region (FIG. 3a) and enlarged details A to C of FIG. 3a (FIG. 3b);

DETAILED DESCRIPTION OF THE INVENTION

Figure 4A:
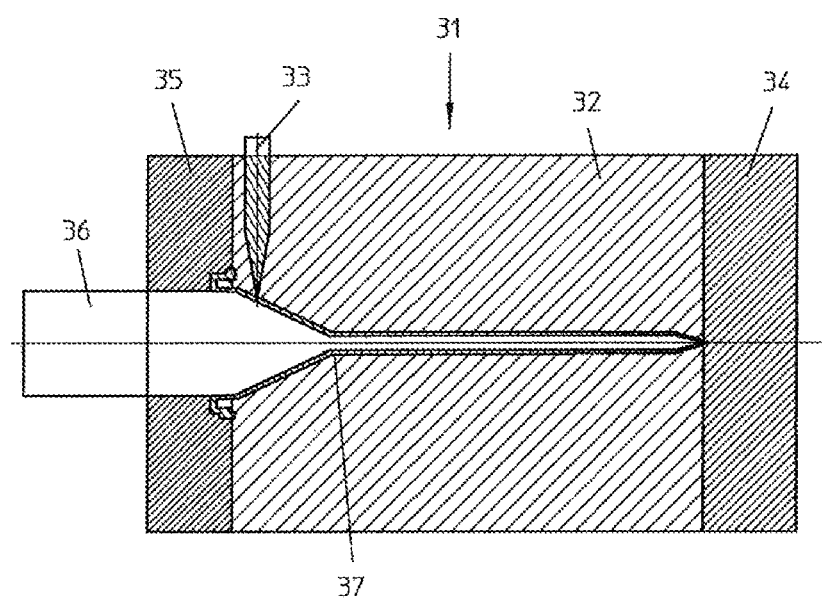
FIGS. 4a and b show the injection-moulding tool for injection-moulding a syringe cylinder of a syringe with a filling volume of 0.1 ml in the closed state when injection-moulding a syringe cylinder (FIG. 4a) and in the open state when ejecting the syringe cylinder (FIG. 4b)

While this invention may be embodied in many different forms, there are described in detail herein a specific preferred embodiment of the invention. This description is an exemplification of the principles of the invention and is not intended to limit the invention to the particular embodiment illustrated In the following description, parts of different exemplary embodiments which correspond to one another are provided with a plurality of reference numerals which are separated by a dot, the numbers positioned before the dot coinciding and the numbers positioned after the dot denoting the respective exemplary embodiment. In summary, parts of different exemplary embodiments corresponding to one another are simply denoted by the numbers which coincide.

According to FIG. 1 a 10 ml syringe 1.1 has a syringe cylinder 2.1 in which a syringe piston 3.1 is arranged. The syringe cylinder 2.1 is not strictly cylindrical overall, in terms of geometry. The syringe cylinder 2.1 has a cylindrical cylinder portion 4.1 on the outside which has a cylindrical piston movement area 5.1 on the inside.

The cylinder portion 4.1 has at the bottom a base 6.1 with a central hole 7.1. The edge of the hole 7.1 is connected to a syringe portion 8.1 which is conical on the inside and outside with a small cone angle, which at the bottom has a cone portion 9.1 which is more conical on the inside and outside. The syringe portion 8.1 and the cone portion 9.1 taper downwards.

The cylinder portion 4.1 is connected at the top via a short transition region 10.1 which is conical on the inside and outside to a centering region 11.1 which is cylindrical or slightly conical on the inside and outside.

The centering region 11.1 is connected at the top to a centering flange 12.1 which has a substantially circular disc-shaped bearing portion 13.1 and a substantially cylindrical peripheral portion 14.1. The bearing portion 13.1 has a bearing surface 15.1. This may have coding in the form of axially aligned scanning surfaces, which are arranged at one or more defined positions. The coding may be designed as described in EP 0 657 216 B1 and U.S. Pat. No. 5,620,661. The explanations of the exemplary embodiments relative thereto from the published patent specifications denoted above are included in the present patent application.

In addition, the syringe cylinder 2.1 above the centering region 11.1 has a conical insertion region 16.1 which widens upwards.

In the cylinder portion 4.1, the base 6.1, the syringe portion 8.1 and the transition region the syringe cylinder 2.1 has an approximately uniform wall thickness.

The syringe cylinder 2.1 is produced in one piece from plastics material. Preferably, it is produced by injection-moulding a thermoplastic. The thermoplastic is, for example, polypropylene; polyethylene or a cyclic olefin (Co)polymer, polypropylene being preferred due to its properties of stability.

The syringe piston 3.1 has a planar cylindrical and/or circular disc-shaped piston portion 17.1 which has on the circumference a peripheral sealing lip 18.1. At the bottom, the piston portion 17.1 is connected to a piston syringe portion 19.1 which is configured conically therewith or with a similar small cone angle as the syringe portion 8.1.

The syringe piston 3.1 is provided at the top with a piston rod 20.1. The piston rod 20.1 has at the top a coupling piece 21.1. The coupling piece 21.1 has a plurality of peripheral piston flanges 22.1 projecting radially, between which peripheral grooves 23.1 are present.

Below the coupling piece 21.1 on the piston rod 20.1 a disc 24.1 is arranged which is configured in the shape of a circular disc.

Below the disc 24.1 on the piston rod 20.1 are located four radially projecting wings 25.1 which are distributed evenly over the periphery of the piston rod 20.1. At the top, the wings 25.1 are connected to the disc 24.1 and at the bottom to the piston portion 17.1. The wings 25.1 have adjacent to the disc 24.1 outer edges 26.1 which are parallel to the piston rod 20.1. Here the wings 25.1 are at their widest. A first bevel 27.1 follows, within which the width of the wings 25.1 reduces. In turn, an external edge 28.1 follows, which is parallel to the piston rod 20.1. At the bottom, the wings 25.1 have a further bevel 29.1 within which the width of the wings 25.1 reduces further.

The syringe piston 3.1 is preferably produced in one piece from plastics material. Further preferably, it is injection-moulded from a thermoplastic. For example, it is produced from polyethylene or polypropylene, polyethylene being preferred, as the material pairing of polyethylene in the piston and polypropylene in the cylinder has low frictional force. Polypropylene is preferred for the cylinder due to its high strength.

The cylindrical portions and regions of the syringe cylinder 2.1 and of the syringe piston 3.1 are circular cylindrical.

If the piston 3.1 is fully inserted into the syringe cylinder 2.1 the piston portion 17.1 is positioned on the base 6.1 and between the piston syringe portion 19.1 and the syringe portion 8.1 a small annular gap remains. The outer edges 26.1 extend from the upper end of the piston movement area 5.1 via the transition region 10.1 into the centering region 11.1. The disc 24.1 engages at the bottom in the centering region 11.1. Between the outer edges 26.1 and the piston movement area 5.1 a small annular gap remains, so that the outer edges 26.1 prevent the syringe piston 3.1 from tilting in the syringe cylinder. Between the disc 24.1 and/or the outer edges 26.1 and the centering region 11.1 a slightly larger annular gap 290.1 is present. The coupling piece 21.1 is partially arranged in the centering region 11.1 and projects over the centering flange 12.1 at the top.

The above information is also applicable in principle for syringes 1.2 to 1.7 with different filling volumes. Particularities of the syringes 1.2 to 1.7 are revealed from the following description:

According to FIG. 2 a 0.1 ml syringe 1.2 has a syringe cylinder 2.2 and a syringe piston 3.2. The syringe cylinder 2.2 is not strictly cylindrical overall, in terms of geometry. It has at the bottom a cylinder portion 4.2 which is cylindrical inside and outside, which has a cylindrical piston movement area 5.2 inside.

The lower end of the cylinder portion 4.2 is connected to a syringe portion 8.2 which is conical on the inside and outside, which is configured as a more conical cone portion 9.2.

The upper end of the cylinder portion 4.2 is connected to a transition region 10.2 which is conical on the inside and outside. The upper end of the transition region 10.2 is connected to a centering region 11.2 which is cylindrical on the inside and outside.

The centering region 11.2 is, in turn, connected at the upper end to a centering flange 12.2. The centering flange 12.2 has a substantially circular disc-shaped bearing portion 13.2 which on the inner edge is connected to the centering region 11.2. In addition, the centering flange 12.2 has a substantially cylindrical peripheral portion 14.2 which at the upper end is connected to the outer edge of the bearing portion 13.2.

The bearing portion 13.2 has at the top a bearing surface 15.2 which may comprise coding corresponding to the bearing surface 15.1.

The syringe piston 3.2 has a long cylindrical piston portion 17.2, which at the bottom has a peripheral sealing lip 18.2 on the periphery. The piston portion 17.2 is connected at the bottom to a piston syringe portion 19.2, which at the top has a cylindrical part and at the bottom a conical part.

The piston portion 17.2 is provided at the top with a piston rod 20.2, which at the top has a coupling piece 21.2, which is formed according to the coupling piece 21.1.

A disc 24.2 is arranged below the coupling piece 21.2 on the piston rod 20.2. Below the disc 24.2 four wings 25.2 protrude radially from the piston rod 20.2, which are evenly distributed over the periphery of the piston rod 20.2. The wings 22.1 are connected at the top to the underside of the disc 24.2 and terminate at the bottom just above the piston portion 17.2 They have at the top in each case outer edges 26.2 parallel to the piston rod portion 20.2, and at the bottom in each case a bevel 27.2.

When the piston 3.2 is fully inserted into the syringe cylinder 2.2, the bevels 27.2 are positioned inside on the transition region 10.2. Between the piston syringe portion 19.2 and the cone portion 9.2 of the syringe cylinder 2.2 a small annular gap remains. The disc 24.2 is arranged at the bottom in the centering region 11.2. Between the centering region 11.2 and the disc 24.2 a small annular gap 290.2 is present. The coupling piece 21.2 is partially arranged in the centering region 11.2 and protrudes at the top beyond the centering flange 12.2.

According to FIGS. 1a and 2a, the syringes 1.1, 1.2 have on the periphery of their centering flanges 12.1, 12.2 alignment lugs 30.1, 30.2 protruding radially outwardly, which taper upwards. The alignment lugs 30.1 and 30.2 have at the top a parabolic contour. In the example, in each case seven alignment lugs 30.1, 30.2 are evenly distributed over the periphery of the centering flanges 12.1, 12.2.

According to FIGS. 1e and 2e, the centering region 11.1, 11.2 at the top has an internal diameter a of 16.2 to 17.7 mm, and extends as far as a depth d of 6 mm. In addition, the piston movement area 5.1, 5.2 has an internal diameter b of 15.96 and/or 1.60 mm. The centering flange 12.1, 12.2 has a height e of 3.2 to 5.4 mm, as well as an external diameter b of 21 to 24.2 mm. The coupling piece 22.1, 22.2 protrudes relative to the centering flange 12.1, 12.2 by approximately 13.5 mm. In the region of the piston flange 22.1, 22.2, the coupling piece 21.1, 21.2 has a diameter g of 7 to 7.2 mm and in the region of the grooves 23.1, 23.2 a diameter h of preferably less than 5 mm. This region is designed for reducing the mass, preferably as a crossed projection structure.

In FIG. 1g, specific dimensions of the centering region 11.1 of the 10 ml syringe 1.1 are provided. Accordingly, the centering region 11.1 has a minimum diameter of 16.2 mm and a maximum diameter of 17.7 mm. The centering region 11.1 starts at a distance of 3 mm from the upper face of the centering flange 12.1 and extends over an axial length of 3 mm. In FIG. 1g, the centering region 11.1 is shown without cross hatching, although the syringe cylinder 2.1 is also vertically sectioned in the centering region 11.1.

FIG. 1h also shows the syringe cylinder 2.1 in vertical section, in which the centering region 11.1 is shown without cross hatching, as said centering region may in principle adopt different geometries. Preferred embodiments of this freeform surface or control form surface are shown in partial section to the right, adjacent to the vertical section through the entire syringe cylinder 2.1. Overall, six geometries are provided, of which three are illustrated in a vertical partial section and a further three in a half-cross section through the centering region 11.1.

The uppermost vertical partial section shows a conically formed centering region 11.11. The second vertical partial section shows a centering region 11.12, indicated as convex. The third vertical partial section shows a peripheral and/or partially peripheral centering region 11.13 provided with (optionally circular) ribs or projections. This last type of embodiment may also serve as a demoulding aid.

The lowermost, blank vertical partial section serves for illustrating the viewing direction from below through the syringe cylinder 2.1 towards the centering region 11.1 which may be configured with different geometries. Different embodiments are thus shown far right in the half-cross sections. Half-cross sections are shown as the cross sections are through the vertical section through the syringe cylinder 2.1 shown adjacent to the left.

The uppermost half-cross section shows a flattened centering region 11.14 intersected by a plurality of secants. The central half-cross section shows a centering region 11.15 provided with protrusions and/or studs and/or projections. The lowermost half-cross section shows an elliptically sectioned centering region 11.16.

It is the case in all these embodiments of the centering region 11.1 that the smallest diameter, which is at a distance of at least 3 and preferably a maximum of 6 mm below the upper face of the centering flange 12.1, is a maximum of between 16.2 and 17.7 mm. The external diameter of a centering ring—explained further below—for centering the centering region also has to have these dimensions, as otherwise the centering ring would not fit in the centering region and would not be able to fulfil its function. This is indicated on the centering region 11.14, by a radius being illustrated there.

These embodiments and dimensions also apply to all further syringes 1.3 to 1.7 of the syringe family explained below.

According to FIG. 3, the further syringes 1.3 to 1.7 of the syringe family with the filling volumes 5 ml, 2.5 ml, 1 ml, 0.5 ml and 0.2 ml are of corresponding construction. The parts of the further syringes 1.3 to 1.7 which correspond to those of the syringes 1.1, 1.2 described above, are provided with corresponding reference numerals, the number provided before the dot coinciding and the number provided after the dot denoting the respective syringe.

In FIG. 3b, the flow brakes below the centering regions 11.1, 11.2, 11.3 are illustrated. Accordingly, between the centering regions 11.1, 11.2, 11.3 and the transition regions 10.1, 10.2, 10.3 corners are present in which during injection-moulding the plastics mass is deflected, so that they form a flow brake. Additionally, the centering regions 11.1, 11.2, 11.3 have a thinner wall thickness than the adjacent transition regions 10.1, 10.2, 10.3. In the 10 ml syringe, the centering region 11.1 has a greater internal diameter than the piston movement area 5.1. As a result, during injection-moulding, pressure losses are produced, which have the result of a uniform filling of the cylinder portions 4.1, 4.2, 4.3 with the hot plastics mass.

In FIG. 4, an injection-moulding tool 31 has a tool plate 32 with a hot channel nozzle 33, a tool cover plate 34 and a stripper plate 35. In addition, it has a tool insert 36. Between the components denoted above, a hollow space 37 is formed which describes the contour of a 0.1 ml syringe cylinder 2.2.

The hot plastics mass is injected through the hot channel nozzle 33 into the hollow space 37. Due to the flow brake between the transition region 10.2 and the centering region 11.2, the transition region 10.2 and the cylinder portion 4.2 of the syringe cylinder 2.2 are evenly filled, so that the syringe cylinder 2.2 has very good dimensional stability at that point. The fact that the transition region 10.2 is injection-moulded contributes thereto, as the tool insert 36 has a relatively large diameter, so that disadvantageous lateral deflection of the tool insert 36 does not occur, which would lead to non-uniform wall thicknesses.

According to FIG. 4b, the injection-moulded syringe cylinder 2.2 is ejected from the injection-moulding tool 31, by the stripper plate 35 being removed from the tool plate 32 and the tool insert 36 being pulled out of the deflection plate 35. The moulded part 2.2 then falls out of the tool 31.

Figure 5:
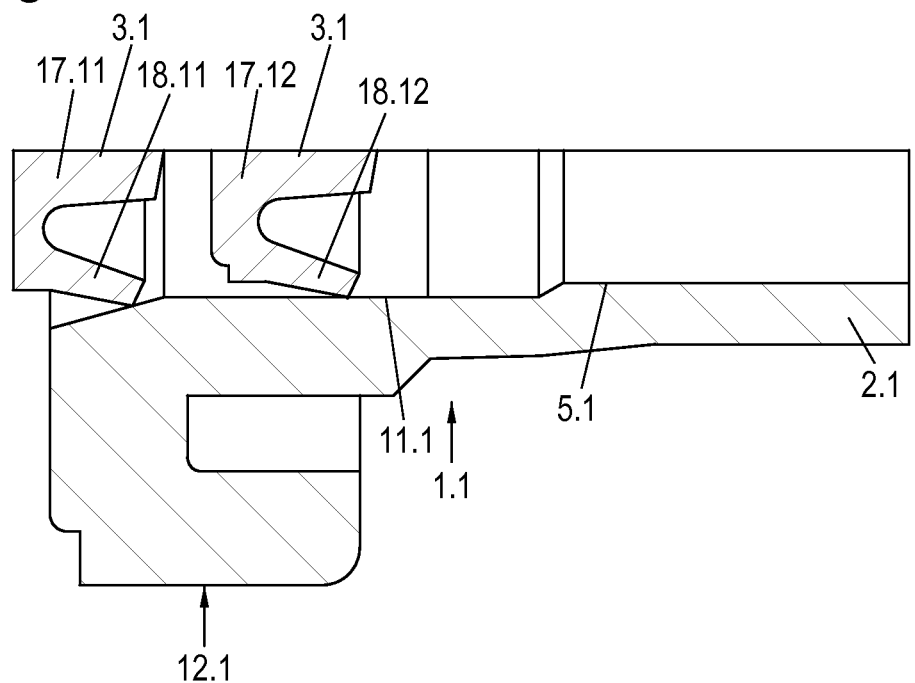
FIG. 5 shows a syringe with a filling volume of 10 ml with syringe piston in two different insertion positions in a full vertical section.
Figure 6:
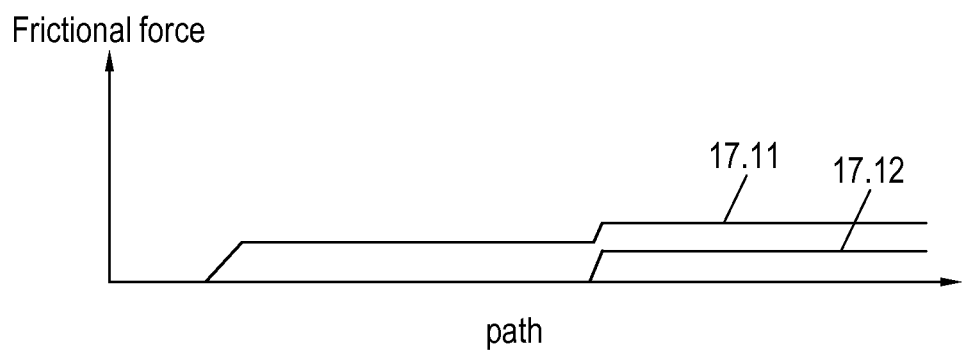
FIG. 6 shows force for inserting two syringe pistons with different dimensions due to production variations in the syringe cylinder of a syringe of FIG. 5, depending on the path of insertion in the force/path diagram.

FIGS. 5 and 6 show how the step change of the internal diameter between the centering region 11.1 and the piston movement area 5.1 of the 10 ml syringe 1.1 may be used for detecting non-dimensionally stable syringe pistons 3.1, in which the external diameter of the piston portion 17.1 in the region of the sealing lip 18.1 exceeds the tolerance upper limit. The internal diameter of the centering region 11.1 is designed so that it corresponds to the tolerance upper limit of the external diameter of the sealing lip 18.1. The internal diameter of the piston movement area 5.1 is 15.96 mm. Hereinafter, corresponding parts of different syringe pistons 3.1, the dimensions thereof differing due to production tolerances, are differentiated by reference numerals, which in the second position after the dot have a different number.

The diameter of the sealing lip 18.11 illustrated in FIG. 5 in the left-hand position is too large. According to FIG. 6, when inserting this piston portion 17.11 two force increments are detected by a dynamometer (load cell) incorporated in the insertion mechanism. As a result, it is clearly indicated that a syringe piston 3.1 which is too large is present. The absence of dimensional stability may, in particular, be based on a non-circularity of the piston portion 17.11, which results in an excessive external diameter of the sealing lip 18.11, which may be established by the test method described above. The piston portion 17.12 shown in FIG. 5 in the right-hand position is, together with the sealing lip 18.12, within the tolerances or too small. According to FIG. 6 only one single force increment is measured in this syringe piston 3.1.

Figure 7:
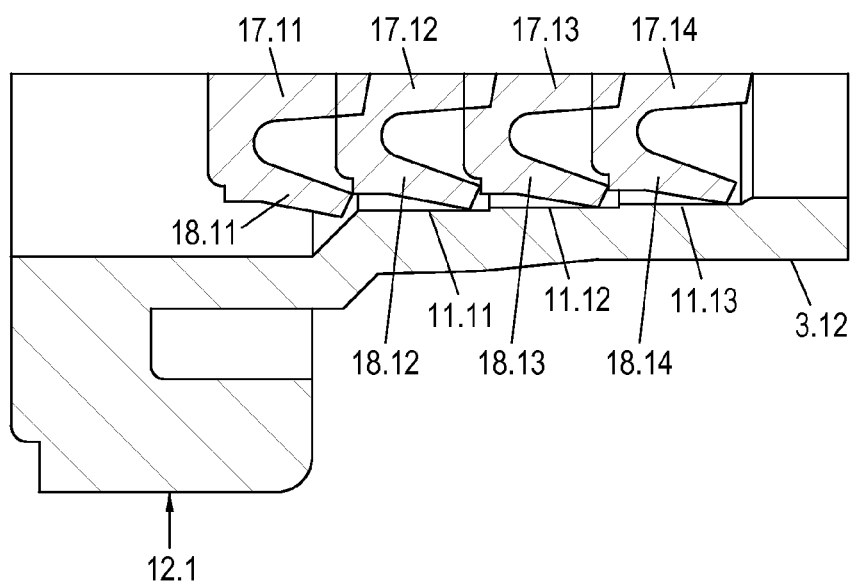
FIG. 7 shows a syringe with a centering region consisting of three substantially cylindrical centering portions, which are used as test diameters and a syringe piston in four different insertion positions in a full vertical section.
Figure 8:
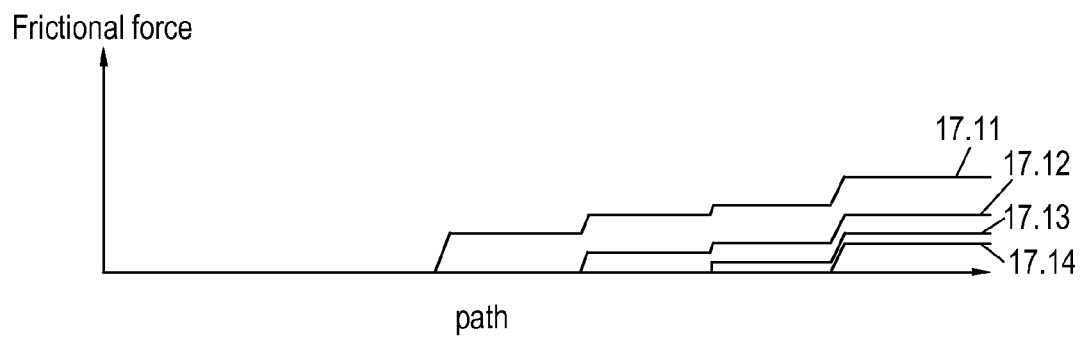
FIG. 8 shows the force for the insertion of four syringe pistons with different dimensions due to production variations in the syringe cylinder of a syringe of FIG. 7, depending on the path of insertion in a force/path diagram.

FIGS. 7 and 8 show a further embodiment by which it may be easily established whether the piston portion 17.1 falls below the tolerance limits. This embodiment has a centering region consisting of three centering portions 11.11, 11.12, 11.13, the internal diameter of the centering portion 11.12 being smaller than the internal diameter of the centering portion 11.11 and the internal diameter of the centering portion 11.13 being smaller than the internal diameter of the centering portion 11.12. Adjoining the centering portion 11.13 is a piston movement area 5.1, the internal diameter of the piston movement area 5.1 in turn being smaller than the internal diameter of the centering portion 11.13.

The internal diameters are designed so that the internal diameter of the centering portion 11.11 corresponds to the tolerance upper limit of the external diameter of the sealing lip 18.1 of the piston portion 17.1. The internal diameter of the centering portion 11.12 corresponds to the lower engagement limit of the external diameter of the sealing lip 18.1 and the internal diameter of the centering portion 11.13 to the lower tolerance limit for the sealing lip 18.1.

The piston portion 17.11 shown to the left in FIG. 7 has on the sealing lip 18.11 an external diameter which is too large. As a result, four force increments may be established in the force/path diagram when inserting this piston portion 17.11.

The piston portion 17.12, shown in FIG. 7 at the second position from the left, has a sealing lip 18.12 with an external diameter at the upper tolerance limit. When inserting this piston portion 17.12, according to FIG. 8 three force increments may be measured. This syringe piston 3.1 is within the tolerance range.

The piston portion 17.13 shown in FIG. 7 at the third position from the left, has on the sealing lip 18.13 an external diameter at the lower tolerance limit. According to FIG. 8, when inserting this piston portion 17.13 two force increments may be seen. This syringe piston 3.1 is still within the tolerance range.

The piston portion 17.14 shown to the right in FIG. 7 has on the sealing lip 18.14 an external diameter which is too small, but which exceeds the internal diameter in the piston movement area 5.1. When inserting this piston portion 17.14 according to FIG. 8 a single force increment may be measured. This syringe piston 3.1 is too small.

The centering portions 11.11 to 11.13 may also be denoted as test portions. This is, in particular, the case when only one part of the centering portions 11.11 to 11.13 is used for centering. In principle, however, all centering portions 11.11 to 11.13 may be used for the centering. The centering is explained in more detail below.

Figure 9:
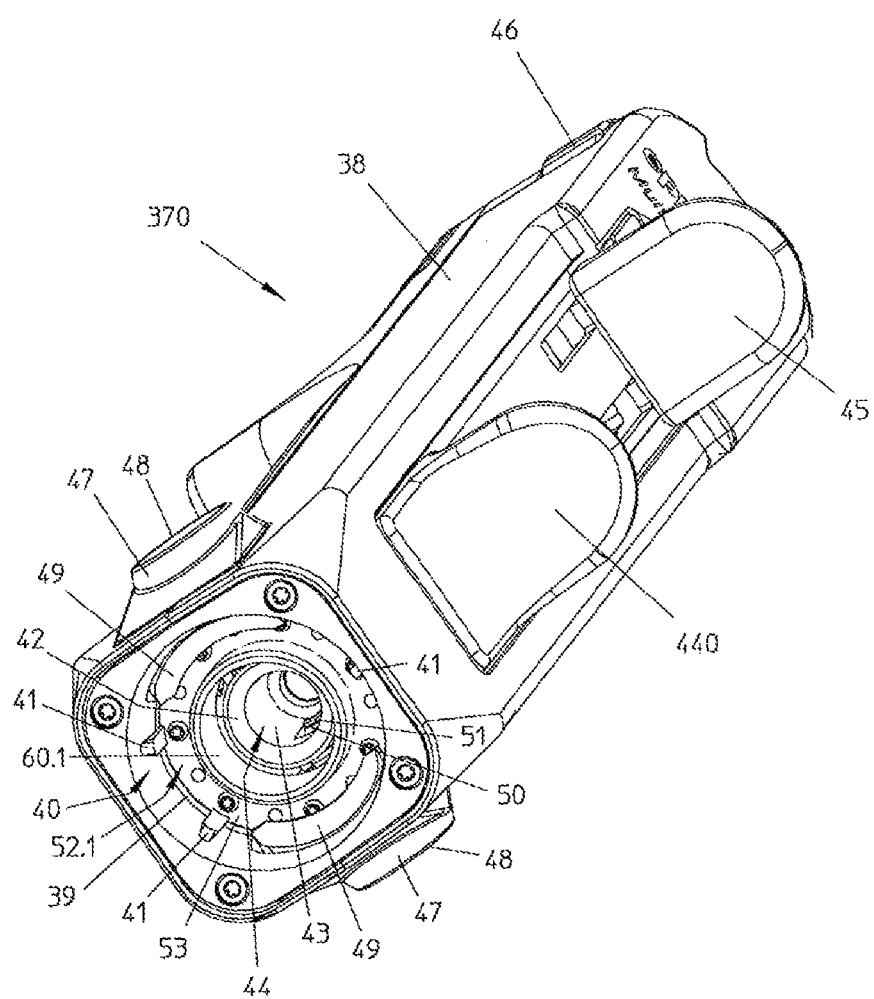
FIG. 9 shows a metering device, in particular dispenser for the use of syringes according to FIGS. 1 to 8, in a perspective view obliquely from below and from the side.

According to FIG. 9, a metering device 370 according to the invention has a housing 38 configured as an elongate handle. At the lower end of the housing 38, a substantially cylindrical receiver 39 is present for the centering flange 12 of the syringe cylinder 2. The receiver 39 is accessible from outside through a circular opening 40 at its lower end. A plurality of axially aligned guide lugs 41 protrude radially inwards on the periphery of the receiver 39.

In addition, in the housing 38 a receiving body 42 is present with a substantially cylindrical piston receiver 43 for a coupling piece 21 of a syringe piston 3. The piston receiver 43 is accessible from outside through a further circular opening 44 at its lower end.

The receiving body 42 is able to be displaced axially in the housing 38 by means of a repeating mechanism, not shown. The repeating mechanism may, in particular, be designed as disclosed in DE 29 26 691 C2 and U.S. Pat. No. 4,406,170 or DE 43 41 229 C2 and U.S. Pat. No. 5,620,660. The explanations relative thereto of the exemplary embodiments from the different published patent specifications are included in the present patent application.

The repeating mechanism comprises a lifting lever 440, which may be axially displaced on the outside of the housing 38, in FIG. 9 the lifting lever 440 being shown in the lowermost position. Accordingly, the receiving body 42 is also located in the lowermost position, in which its lower end is arranged approximately level with the base of the receiver 39.

In addition, the repeating mechanism comprises a metering lever 45 which protrudes at the top from the housing 38 and is pivotably mounted in the housing 38. The metering lever 45 is loaded by a spring device so that it is forced into its uppermost position. By pivoting the metering lever 45 downwards, the receiving body 42 may be displaced downwards by a metering stage. The increment of the metering stage is able to be adjusted by means of a knurled adjusting wheel 46 which is located at the upper end of the housing 38.

In addition, two diametrically opposed syringe gripping levers 47 are arranged at the bottom in the housing 38. The syringe gripping levers 47 are mounted pivotably in the housing 38. The syringe gripping levers 47 have actuating buttons 48 protruding outwardly from the housing 38. They penetrate through-holes in the housing 38 and have hook-like cylinder gripping ends 49 protruding into the receiver 39.

In addition, two piston gripping levers 50 are mounted diametrically opposing one another in the receiving body 42. The piston gripping levers 50 penetrate through-holes in the receiving body 42 so that they engage with hook-like piston gripping ends 51 into the piston receiver 43.

The syringe gripping levers 47 and piston gripping levers 50 are in each case designed to be double-armed with a gripping arm and an actuating arm, and pivotably mounted in the connecting region of the gripping arm and the actuating arm. In addition, the syringe gripping levers 47 on the inner faces of their actuating arms have unlocking cams and the piston gripping levers 50 on the actuating arms have cam-like projections. Spring elements, not shown, load the syringe gripping levers 47 and the piston gripping levers 50 so that said levers in each case are pivoted towards one another with their cylinder gripping ends 49 and/or piston gripping ends 51. The construction corresponds to the exemplary embodiment according to DE 43 41 229 C2 and U.S. Pat. No. 5,620, 660. The embodiments relevant thereto from the published patent specifications denoted above are included in the present patent application.

Figure 10:
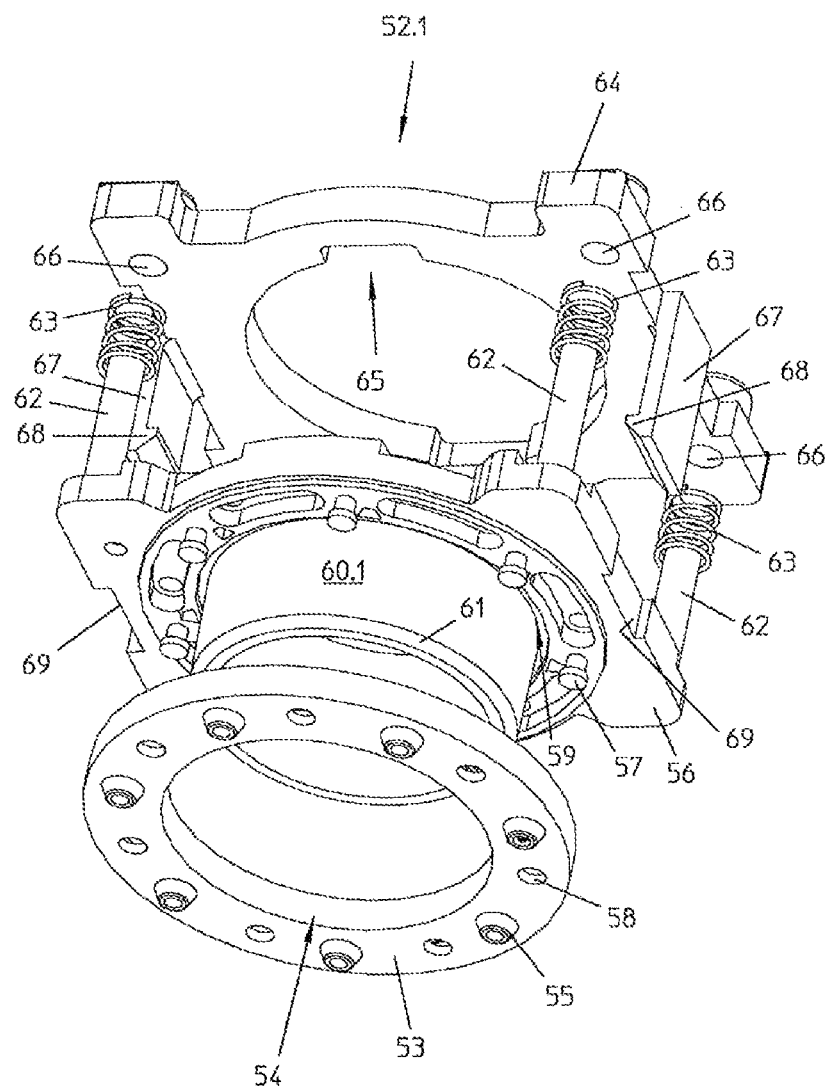
FIG. 10 shows the resilient upper stop with a centering element with an axial through-passage of the same metering device in an enlarged perspective exploded view.
Figure 11:
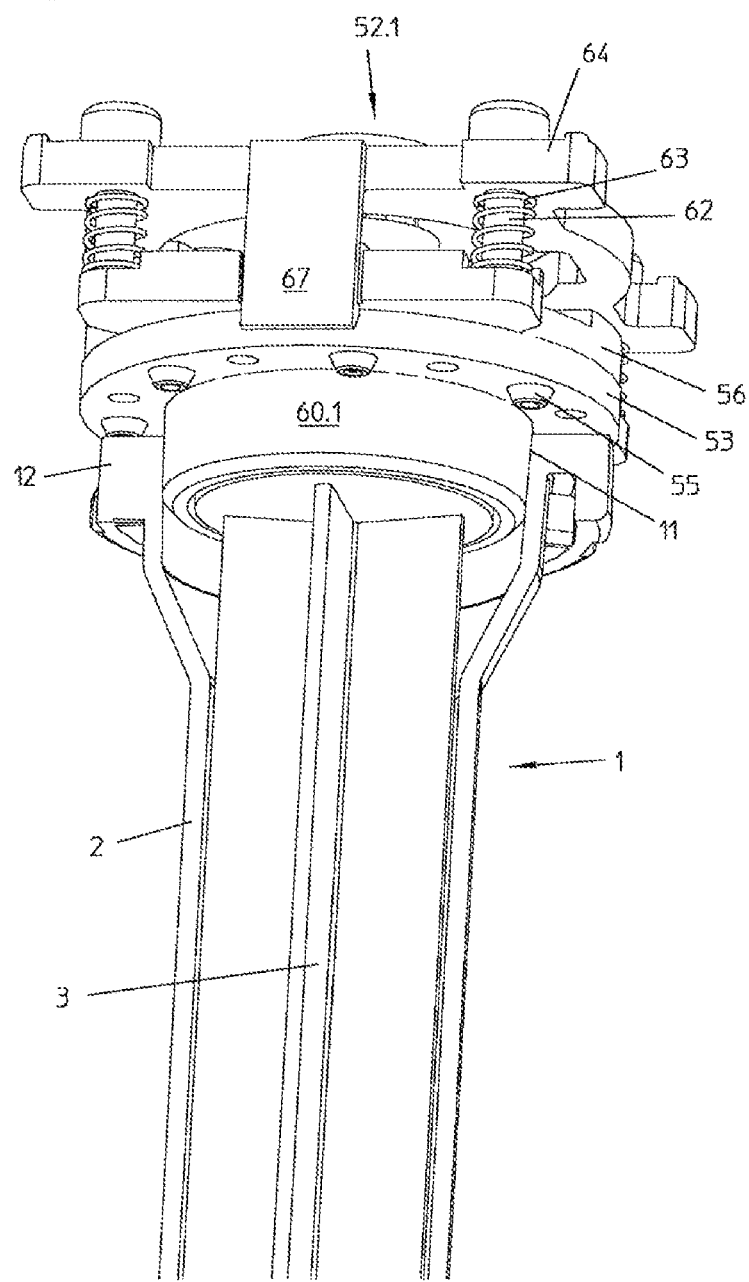
FIG. 11 shows the same resilient upper stop with the centering element combined with an axial through-passage with the adjacent syringe in an enlarged perspective view of the syringe cylinder in full vertical section.

At the base of the receiver 39 a sensor device 52.1 is present for coding on a centering flange 12 of a syringe 1, which is shown in FIGS. 10 and 11. The sensing device 52.1 has an annular disc-shaped sensor plate 53 with a central hole 54 and seven axially protruding studs 55 which are evenly distributed over the underside of the sensor plate 53. Each stud 55 is operatively connected to a micro-switch arranged in the sensor plate 53. As a result of the actuation of a stud 55, the micro-switch operatively connected thereto is actuated.

In addition, the sensor device 52.1 comprises a support plate 56 for the sensor plate 53. The sensor plate 53 is able to be fixed to the support plate 56 by means of bolts 57, which penetrate the holes 58 of the sensor plate 53.

The support plate 56 has a central hole 59, the diameter thereof corresponding to the diameter of the hole 54 of the sensor plate 53. On the internal periphery of the hole 59 of the support plate 56 a circular hollow cylindrical centering element 60.1 (also known as the "centering tube") is fixed with an axial through-passage which on the lower edge has a chamfer 61 on the outside. The centering element 60.1 engages through the hole 54 of the sensor plate 53, when the sensor plate 53 is fixed by means of the bolt 57 to the support plate 56.

From the upper face of the support plate 56, pins 62 protrude, in each case a pin 62 being arranged on a corner. The pins 62 are fixedly connected to the support plate 56.

Helical springs 63 are guided on the pins 62.

In addition, a retaining plate 64 is present which also has a central hole 65, the diameter thereof approximately corresponding to the diameter of the holes 54, 59. The retaining plate 64 has at the corners in each case a bore 66 into which in each case a pin 62 of the support plate 56 may be inserted.

When the pins 62 are inserted into the bores 66, the helical springs 63 are arranged with slight pretensioning between the support plate 56 and the retaining plate 64. This state is shown in FIG. 11.

In addition, the retaining plate 64 has on opposing sides axially oriented spring hooks 67 with in each case a hook end 68, which when joining together the support plate 56 and retaining plate 64 slide through lateral grooves 69 of the support plate 56 and finally engage with the hook ends 68 over the underside of the support plate 56. This is also shown in FIG. 11. The spring hooks 67 hold the arrangement consisting of the support plate 56 and the retaining plate 64 together.

The arrangement shown in FIG. 11 permits the support plate 56 and the retaining plate 64 to be sprung together.

Details of a sensor plate 53 are disclosed in the exemplary embodiment of EP 0 657 216 B1 and U.S. Pat. No. 5,620,661. The embodiments relevant thereto in the aforementioned published patent specifications are included in the present patent application.

According to FIG. 11, a syringe 1 is positioned on the sensor device 52.1. The syringe 1 bears with the upper face of the centering flange 12 against the sensor plate 53. Thus a code arranged on the bearing surface may be detected by means of the studs 55.

The centering element 60.1 with an axial through-passage engages in the centering flange 12. Thus the centering element 60.1 bears with the axial through-passage against the cylindrical centering region 11.

The arrangement described above consisting of the sensor plate 53, the support plate 56, the centering element 60.1 with an axial through-passage and retaining plate 64 is fitted into the housing 38 of the metering device 370 of FIG. 9. Thus the retaining plate 64 is fixed in the housing 38. The sensor plate 53 forms the base of the receiver 39. From this base the centering element 60.1 protrudes into the receiver 39. The receiving body 42 is accessible from outside through the opening 40 of the receiver and the holes 59 and 65 of the sensing device 52.1.

Figure 12:
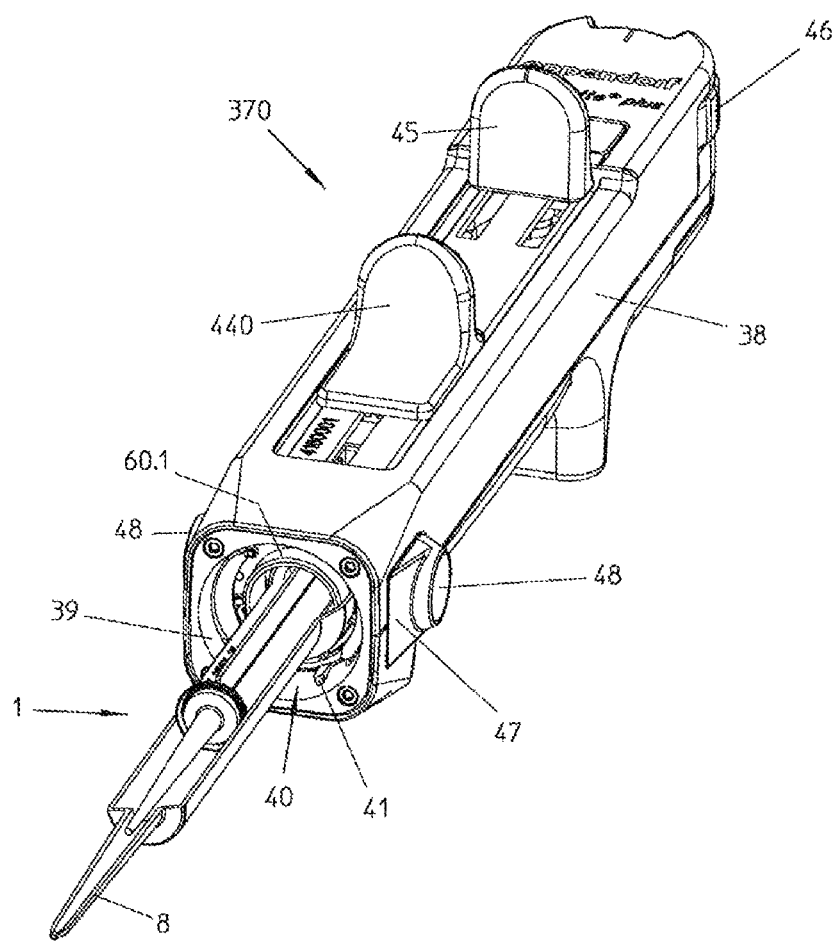
FIG. 12 shows the same metering device with the inserted syringe in a perspective view obliquely from below and from the side with the syringe cylinder in a vertical half-section.

FIG. 12 shows a metering device 370 with a syringe 1 inserted. The syringe 1 is inserted with the centering flange 12 through the opening 40 into the receiver 39. In this connection, the syringe 1 is guided by the alignment lugs 30 on the guide lugs 41, so that the code on the bearing surface 15 is accurately associated with the studs 55. The syringe gripping levers 47 slide over the edge of the centering flange 12 due to the spring action with their cylindrical gripping ends 49, until they snap under the underside thereof. When the bearing surface 15 bears against the sensor plate 53, the centering flange 12 is engaged behind on the underside by the cylinder gripping ends 49 of the syringe gripping levers 47.

When inserting the syringe 1, the receiving body 42 is arranged in its lowest position. In this position, the coupling piece 21 engages in the piston receiver 43. The piston gripping levers 50 slide with their gripping ends 51 over the coupling piece 21 until they snap behind a piston flange 22 into a groove 23.

In addition, when inserting the syringe 1 the centering element with the axial through-passage 60.1 penetrates the centering region 11, so that the syringe 1 is fixed in the metering device 370. As the centering element 60.1 is resiliently mounted, it may easily penetrate the centering region 11, even when the syringe 1 is positioned slightly obliquely on the centering element 60.1.

By means of this centering, the syringe 1 is positioned accurately in its seat in the receiver 39 and the piston receiver 43, so that it is accurately gripped by the gripping devices 47, 50. In addition, the centering element with the axial through-passage 60.1 corrects a possible non-circularity of the syringe cylinder 2. Moreover, the centering element 60.1 holds the syringe 1 in correct alignment, even when the syringe end 8 of the syringe 1 is positioned and a transverse force is introduced into the syringe 1.

Figure 13:
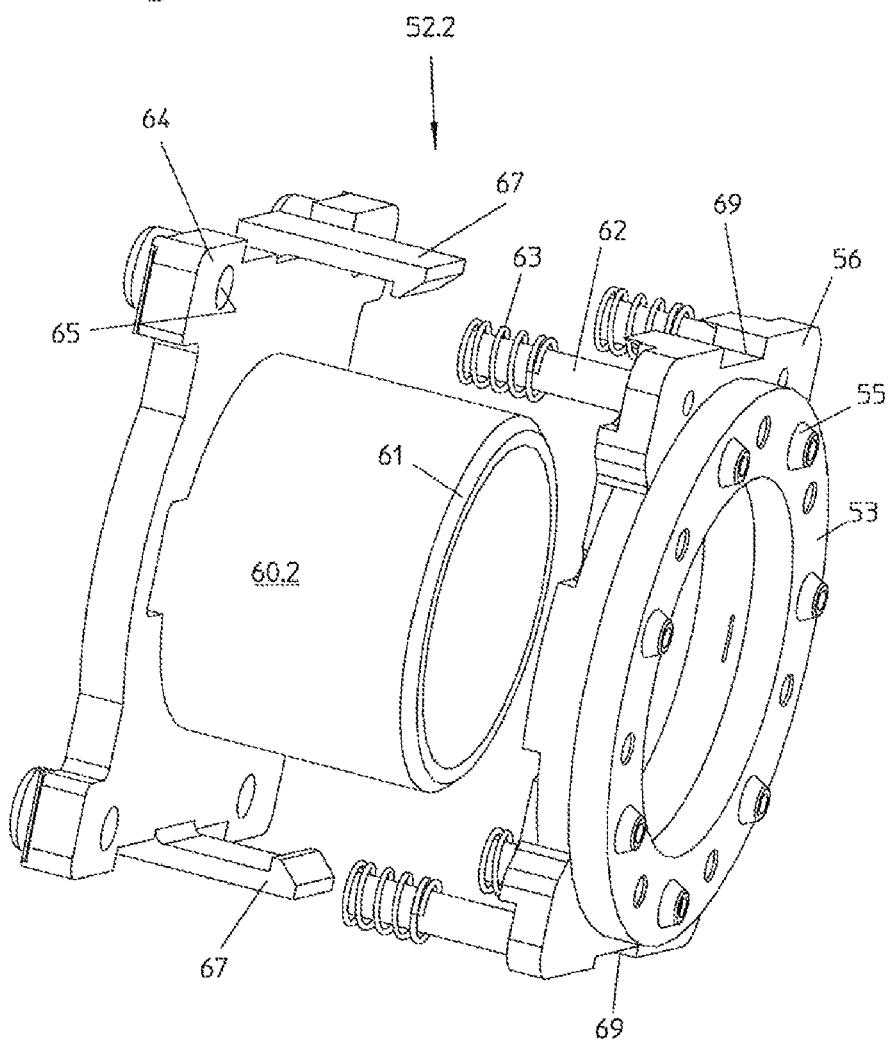
FIG. 13 shows the resilient upper stop of an alternative metering device with the centering element with the axial through-passage arranged rigidly relative to the receiver in a perspective exploded view.

FIG. 13 shows an alternative sensing device 52.2 in which the centering element 60.2 is fixed to a retaining plate 64. The sensing device 52.2 may be mounted in the metering device 370, instead of the sensing device 52.1. In this connection, the retaining plate 64 is fixed in the housing 38. In this embodiment, the syringe 1 is subjected to an even smaller deflection under load by a transverse force.

Figure 14:
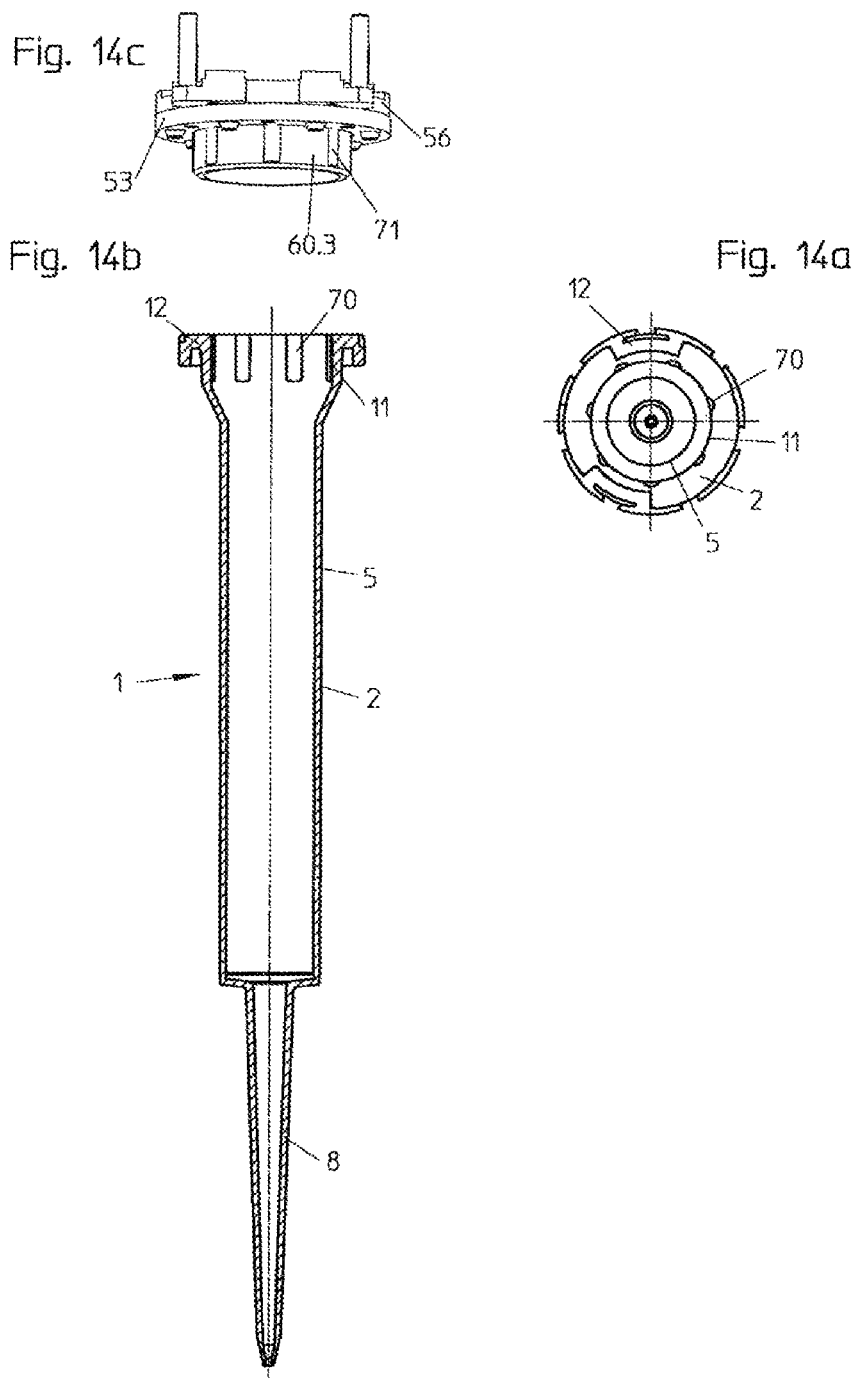
FIGS. 14a to c show syringes with axially extending recesses in the centering region in plan view (FIG. 14a) and in vertical section (FIG. 14b) as well as the centering element with raised portions which are complementary to the recesses in a perspective view obliquely from below and from the side.

According to FIG. 14, a syringe 1 has in the centering region 11 axially extended grooves 70. In addition, the centering element with the axial through-passage 60.3 has externally on the periphery axially extended ribs 71, which fit into the grooves 70. When the syringe 1 is pushed onto the centering element 60.3, the interlocking of the grooves 70 and ribs 71 prevents twisting of the syringe 1 relative to the receiver 39. As a result, damage to the sensor plate 53 is avoided.

Figure 15:
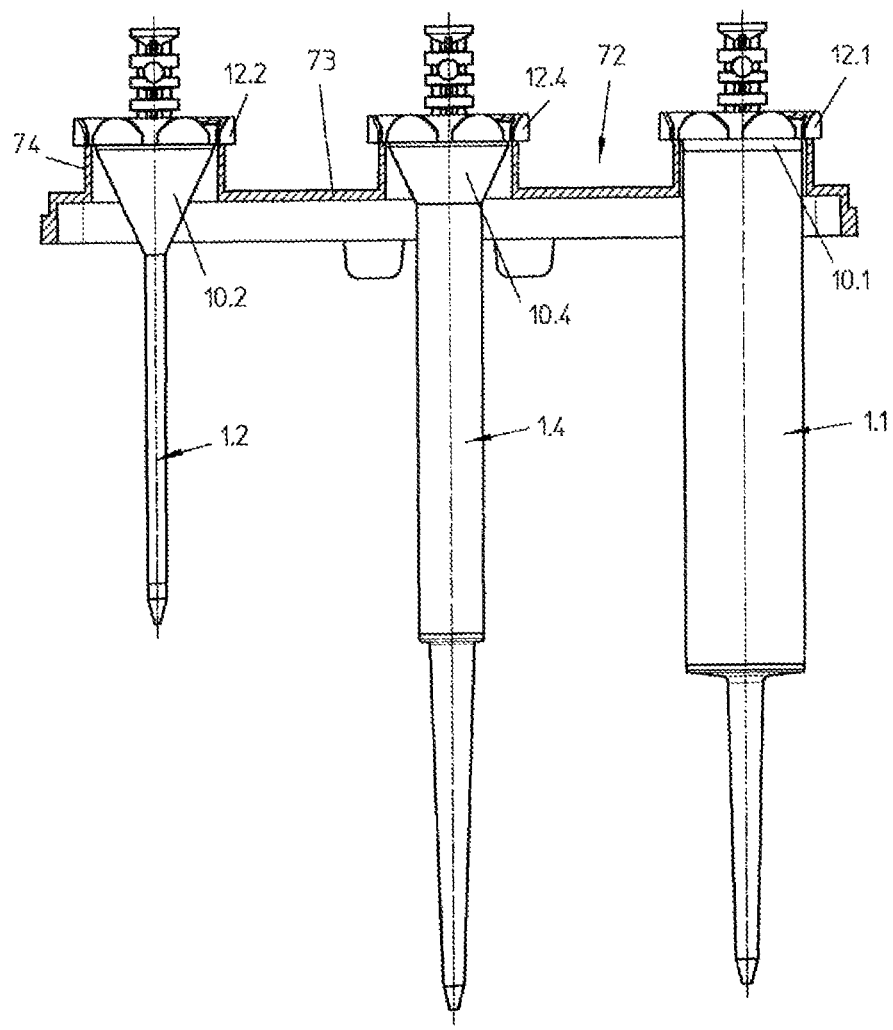
FIG. 15 shows different syringes arranged on a tray for syringes in vertical section.

According to FIG. 15 a cover 72 of a box and/or a tray, not shown, has a plate 73, which has a plurality of support sleeves 74 protruding upwards. Syringes 1.1, 1.2, 1.4 of different sizes are positioned with their centering flange 12.1, 12.2, 12.4 at the top on the edge of the support sleeves 74. In this connection they are guided on the external periphery of the centering region 11.1, 11.2, 11.4 in the support sleeves 74. The externally conical transition regions 10.1, 10.2, 10.4 ensure that the syringes 1.1, 1.2, 1.4 are accurately guided into the correct retaining position.

Figure 16:
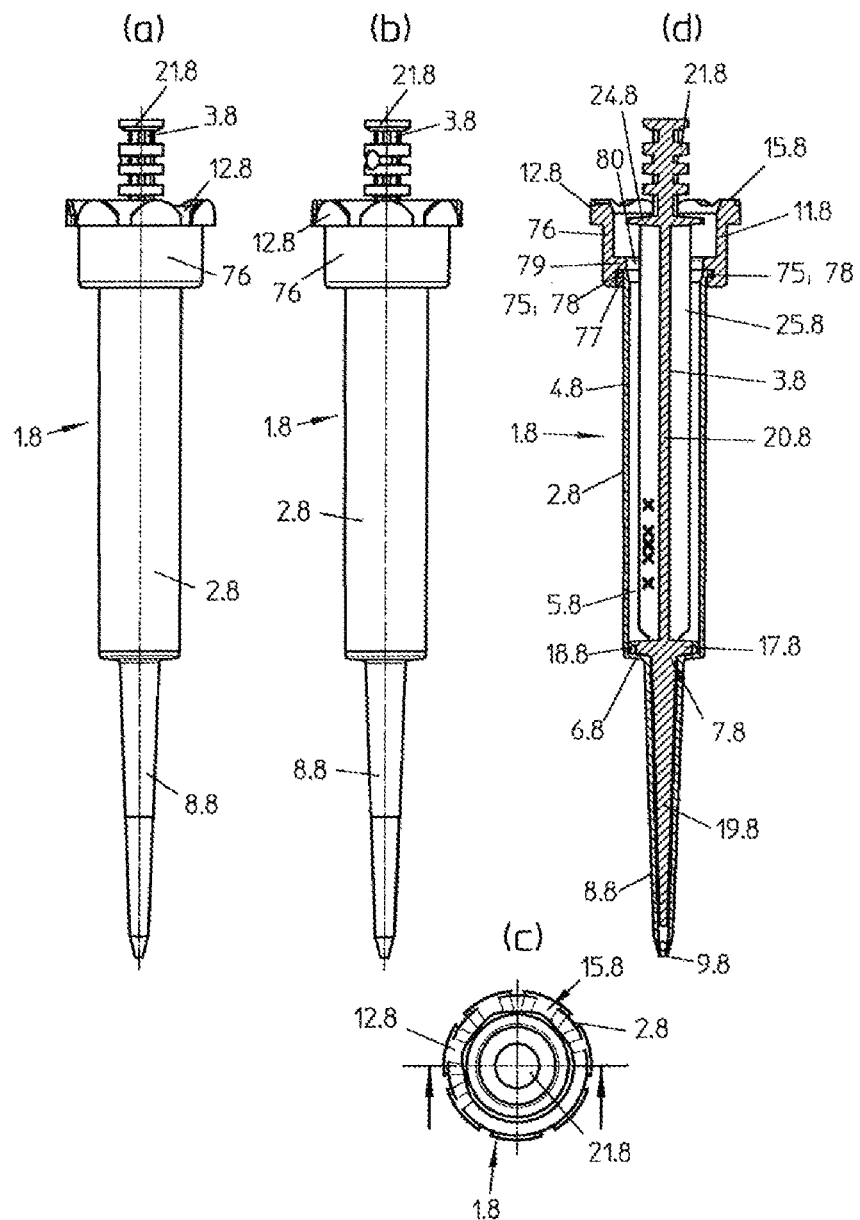
FIGS. 16a to d show a syringe comprising an adapter in side view (FIG. 16a), a side view from the opposing side (FIG. 16b), a plan view (FIG. 16c) and a vertical section (FIG. 16d)

According to FIG. 16 a syringe 1.8 has a syringe cylinder 2.8 with a cylinder portion 4.8, which on the inside has a cylindrical piston movement area 5.8. The cylinder portion 4.8 has at the bottom a base 6.8 with a central hole 7.8, the edge thereof having a conical syringe portion 8.8 which has a more conical cone portion 9.8 at the lower end.

The cylinder portion 4.8 has on the upper edge two diametrically opposing projections 75 of a bayonet connection, protruding radially outwards.

In addition, the syringe cylinder 2.8 has an adapter 76 which is of substantially sleeve-shaped configuration. The adapter 76 has, on the inside, axial grooves 77 of the bayonet connection proceeding from the lower edge, which terminate at an axial distance from the lower edge. The axial grooves 77 are arranged on two diametrically opposing inner faces of the adapter 76. At the top the axial grooves 77 open into peripheral grooves 78 of the bayonet connection.

The syringe cylinder 2.8 is inserted in FIG. 16 with the projections 75 through the axial grooves 77 and rotated into the peripheral grooves 78, as far as the end of the respective peripheral groove 78. By this bayonet connection 75, 77, 78 the syringe cylinder 2.8 is connected to the adapter 76.

The adapter 76 has a centering region 11.8 above an intermediate base 79 which defines the peripheral grooves 78 at the top. The adapter 76 has on the upper edge a centering flange 12.8 protruding radially outwards, which at the top has a bearing surface 15.8 with coding.

The intermediate base 79 has a large through-opening 80 through which a syringe piston 3.8 is inserted into the syringe cylinder 2.8. The syringe piston 3.8 has a piston portion 17.8 with a peripheral sealing lip 18.8 on the periphery. At the bottom, the piston portion 17.8 is connected to a piston syringe portion 19.8 and at the top is provided with a piston rod 20.8. The piston rod 20.8 has at the top a coupling piece 21.8. Below the coupling piece 21.8 the piston rod 20.8 is provided with a disc 24.8 and radially protruding wings 25.8 are positioned therebelow on the piston rod 3.8.

This syringe 1.8 is able to be inserted with the adapter 76 into the receiver 39 and with the coupling piece 21.8 into the receiving body 42 of a metering device 370, as is explained above for the syringe 1 with reference to FIG. 12. In this connection, the adapter is guided by the centering element 60.1 in the centering region so that the syringe 1.8 is centred.

According to the following test report, the deflections of the syringe 1 held in the metering device 370 (see FIG. 12) under load are exceptionally small in comparison with a metering device which has no centering of the syringe.

In the test report, the tested syringes are also denoted as "Combitips®", the tested metering devices also as "Multipette®" and the centering element as "centering tube" or "centering sleeve" or "centering ring".

Object:

The purpose of the test is to what extent the tilting of the Combitip® relative to the Multipette® may be reduced by a centering ring on the Multipette®. Prior art: if when discharging a volume against a receptacle wall the receptacle is pressed too strongly, the Combitip® tilts relative to the Multipette®. In this connection, the Combitip cylinder springs-in on one side with the resilient switching pad. As the piston, however, is not resilient therewith, it may lead to a movement between the Combitip cylinder and Combitip piston. As a result, it may lead in turn to metering errors. If the cylinder tilts too much, an error report is emitted in the Multipette®. This may only be eliminated by moving into the zero position.

Summary:

With a non-resilient centering sleeve (see FIG. 17a) in the Multipette® the force which is required for tilting the cylinder has been increased by 78% relative to a standard Multipette®. In a Multipette® with a resilient centering sleeve (see FIG. 17b) the force which is required for tilting has been increased by 40%.

Objects Tested/Material Tested:

The prototypes have been compared with a standard Multipette® X-stream. For the tests, two Multipettes® have been converted. The switching pads with the receiving plates have been altered as follows.

Figure 17A:
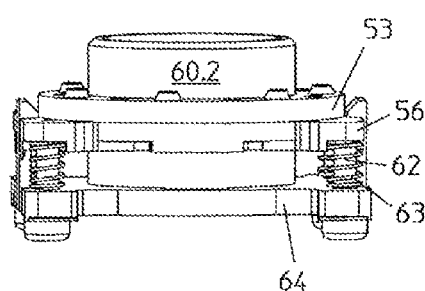
FIGS. 17a and b show a detail of a metering device with a non-resilient centering ring which is connected to the retaining plate (FIG. 17a) and a metering device with a resilient centering ring which is sprung with the support plate (FIG. 17b)
Figure 17B:
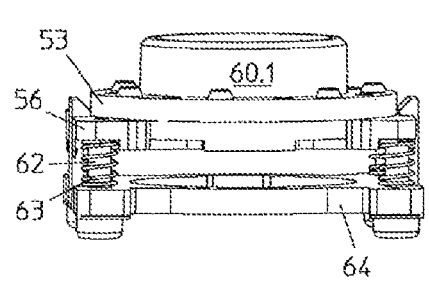

In FIG. 17a, the centering sleeve is shown fastened in a non-resilient manner to the support plate. The arrangement of FIG. 17a corresponds to the arrangement shown in FIG. 13. In FIG. 17b, the centering sleeve is fastened to the base, so that the centering sleeve is resilient therewith. The arrangement of FIG. 17b corresponds to the arrangement shown in FIGS. 10 and 11. The standard components which are used of a dispenser of the Multipette® type have not been altered.

For the measurements, 10 ml Combitip® plus have been used. The centering sleeves have been tailored to this diameter.

Method/Test Method:

The measurements have been carried out on a tension/compression machine (type Z005) from Zwick Roell.

The testing speed was 50 mm/min. The measurements were started after 0.1N initial load.

Figures 18A, 18B:
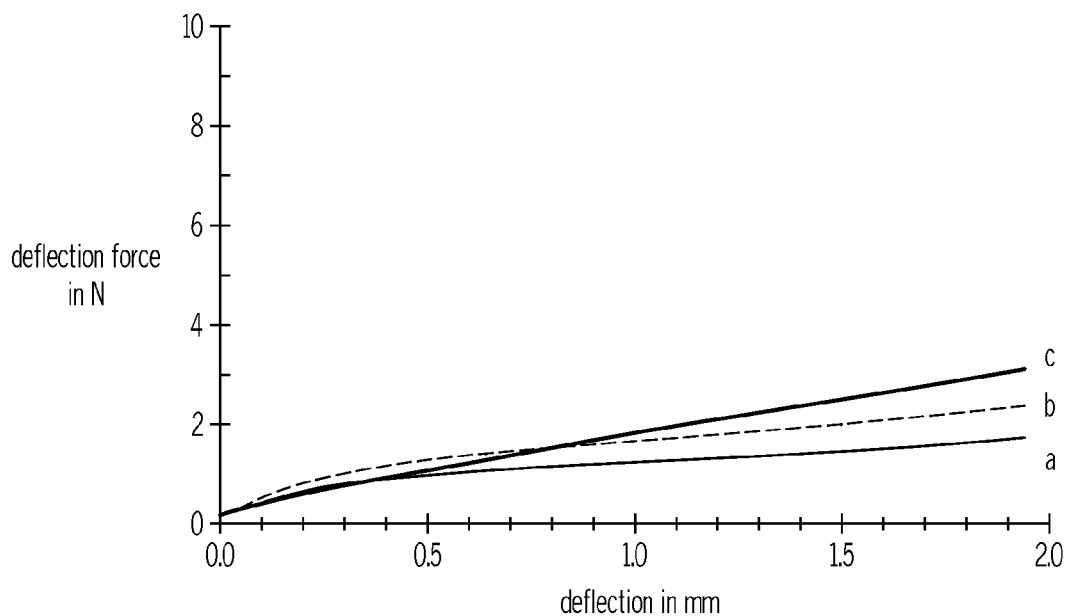
FIGS. 18a and b show a table with measurement results from tests with a conventional dispenser and those with a resilient and/or non-resilient centering element (FIG. 18a) and a graphic representation of the results (FIG. 18b).

Individual Results:

FIG. 18 (table and graphics) shows the comparison of a conventional dispenser of the Multipette® type with a metering device according to the invention with a resilient centering sleeve as well as with a metering device according to the invention with a non-resilient centering sleeve. In the measurements 1 and 2 (see FIG. 18a: table) a standard Multipette® has been used. For the measurements 3 and 4 a prototype Multipette® with a non-resilient centering sleeve—as shown in FIG. 17a—has been used. The measurements 5 and 6 have been carried out with a prototype Multipette® with a resilient centering sleeve—as shown in FIG. 17b. A graphic representation of the results is shown in FIG. 18b, a showing the results with the conventional dispenser, b the results with the dispenser with the resilient centering sleeve and c the results with the dispenser with the non-resilient centering sleeve.

According to the following test report, in a conventional metering system which has no centering of the syringe in the metering device, metering errors are caused by deflection of the syringe as a result of transverse force. Accordingly, with the syringes 1 according to the invention and the metering device 370 considerably more accurate metering is possible.

In the test report the tested syringes are also denoted as "Combitips®", the tested metering devices also as "Multipette®" and the centering element as "centering tube" or "centering sleeve" or "centering ring".

In the above test, the force which is required for tilting the Combitips® has been detected, amongst other things. Background: if when discharging a volume against a receptacle wall the receptacle is pressed too strongly, the Combitip® is tilted relative to the Multipette. In this connection, the Combitip cylinder springs-in with the resilient switching pad on one side. It is now to be tested how great the volumetric error is by tilting the Combitip®.

Summary:

If the Combitip® is tilted by 1 mm relative to the Multipette®—less than 1N force is required therefor—with a volume of 5 ml an error results which may be twice as high as the permissible incorrectness (according to the Eppendorf specification).

Tested Object/Tested Material

The testing has been carried out using a standard Multipette® X-stream and a 50 ml Combitip® plus. For metrological reasons the largest Combitip® has been selected for this test.

Method/Test Method:

The test installation has been extended from the above test by a Mettler AE 163 balance which has been placed under the Combitip®. The Combitip® has been filled with water. By delivering the return stroke via the top, the air bubble has been forced out. Before the measurement, 90% of the water has been discharged again. During the measurements, therefore, the piston was 5 mm above the residual stroke position. For each test, the Combitip® was filled up again. As small volumes discharged at a slow discharge rate are generally collected as droplets at the outlet of the Combitip®, the liquid forced out by the tilting was absorbed by a Kimberly Clark cloth approximately 10 cm$^2$ in size. The collecting container under the inserted Combitip® together with the cloth was weighed before and after the test.

The tension/compression machine, type Z005 from Zwick Roell, has been used with the balance for the measuring installation.

The test speed was 50 mm/min. The measurements were started after 0.1N initial load.

Individual Results

| Deflection | Test | Vol. forced out | Observation | |
|---|---|---|---|---|
| 1 mm | 1 | 0.03 g = 0.03 ml | The droplet forced out remains suspended on the tip | 0.03 ml is approximately a sphere with a 3.9 mm diameter |
| 1 mm | 2 | 0.02 g = 0.02 ml | | |
| 1 mm | 3 | 0.02 g = 0.02 ml | | |
| 2 mm | 4 | 0.055 g = 0.055 ml | One droplet falls, the second remains suspended | 0.065 ml is approximately a sphere with a 5 mm diameter |
| 2 mm | 5 | 0.06 g = 0.06 ml | | |
| 2 mm | 6 | 0.07 g = 0.07 ml | | |

In order to tilt the 50 ml Combitip® relative to the Multipette® X-stream by 2 mm, 1.2 to 1.3N were required.

The Eppendorf specification for the Multipette® X-stream in combination with a 50 ml plus:

| Volume | Incorrectness | Inaccuracy |
|---|---|---|
| 5,000 μl | ±0.3% | ≤0.25% |
| 50,000 μl | ±0.3% | ≤0.15% |

Percentage error with 1 mm deflection:

| | |
|---|---|
| At a volume of 50,000 μl | 0.03 ml/50 ml * 100% = 0.06% |
| At a volume of 5,000 μl | 0.03 ml/5 ml * 100% = 0.6% greater than Eppendorf specification |

Percentage error with 2 mm deflection:

| | |
|---|---|
| At a volume of 50,000 μl | 0.06 ml/50 ml * 100% = 0.12% |
| At a volume of 5,000 μl | 0.06 ml/5 ml * 100% = 1.2% greater than Eppendorf specification |

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

| List of reference numerals | |
|---|---|
| 1 | Syringe |
| 2 | Syringe cylinder |
| 3 | Syringe piston |
| 4 | Cylinder portion |
| 5 | Piston movement area |
| 6 | Base |
| 7 | Hole |
| 8 | Syringe portion |
| 9 | Cone portion |
| 10 | Transition region |
| 11 | Centring region |
| 12 | Centring flange |
| 13 | Bearing portion |
| 14 | Peripheral portion |
| 15 | Bearing surface |
| 16 | Insertion region |
| 17 | Piston portion |
| 18 | Sealing lip |
| 19 | Piston syringe portion |
| 20 | Piston rod |
| 21 | Coupling piece |
| 22 | Piston flange |
| 23 | Groove |
| 24 | Disc |
| 25 | Wing |
| 26 | Outer edges |
| 27 | Bevel |
| 28 | Outer edge |
| 29 | Bevel |
| 290 | Annular gap |
| 30 | Alignment lug |
| 31 | Injection-moulding tool |
| 32 | Tool plate |
| 33 | Hot channel nozzle |
| 34 | Tool cover plate |
| 35 | Stripper plate |
| 36 | Tool insert |
| 37 | Hollow space |
| 370 | Metering device |
| 38 | Housing |
| 39 | Receiver |
| 40 | Opening |
| 41 | Guide lug |
| 42 | Receiving body |
| 43 | Piston receiver |
| 44 | Opening |
| 440 | Lifting lever |
| 45 | Metering lever |
| 46 | Knurled adjusting wheel |
| 47 | Syringe gripping lever |
| 48 | Actuating button |
| 49 | Cylinder gripping ends |
| 50 | Piston gripping lever |
| 51 | Piston gripping ends |
| 52 | Sensor device |
| 53 | Sensor plate |
| 54 | Hole |
| 55 | Stud |
| 56 | Support plate |
| 57 | Bolt |
| 58 | Holes |
| 59 | Hole |
| 60 | Centring element |
| 61 | Chamfer |
| 62 | Pin |
| 63 | Helical spring |
| 64 | Retaining plate |
| 65 | Hole |
| 66 | Bore |
| 67 | Spring hook |
| 68 | Hook end |
| 69 | Grooves |
| 70 | Grooves |
| 71 | Ribs |
| 72 | Cover |
| 73 | Plate |
| 74 | Support sleeves |
| 75 | Projection |
| 76 | Adapter |
| 77 | Axial element |
| 78 | Peripheral groove |
| 79 | Intermediate base |
| 80 | Through-opening |

The invention claimed is:

1. Syringe for use with a metering device (370) comprising a centering element (60) with an axial through-passage in a cylindrical receiver (39) at the lower end of a housing for a syringe cylinder (2) and an axially displaceable piston receiver (43) within the housing for a syringe piston (3), comprising
   a syringe cylinder (2)
   and a syringe piston (3),
   the syringe cylinder (2) comprising an outlet at the bottom and a top,
   a centering flange at the top of said syringe cylinder on an external periphery (12) for inserting into the receiver (39) of a metering device (370),
   said syringe cylinder including a cylindrical piston movement area (5) connected to the outlet, with a first internal diameter, in which the syringe piston (3) is sealingly guided, and
   at least at a distance of at least 3 mm from the upper end of the syringe cylinder a centering region (11) designed for insertion therein of a circular hollow cylindrical centering element (60) of said metering device (370), which has a second internal diameter, which exceeds the first internal diameter and is at least 16.2 mm and at most 17.7 mm,
   and the syringe piston (3) at the upper end has a coupling piece (21) for inserting into a piston receiver (43) of the metering device (370);
   wherein the syringe piston (3) at the top has axially extended wings (25) below a coupling piece (21) and between the wings (25) and a cylindrical centering region an annular gap (290) is present with a gap width of between about 0.5 to 2.5 mm.

2. Syringe according to claim 1, in which the wall thickness of the syringe cylinder (2) in the cylindrical piston movement area (5) is greater than in the centering region (11).

3. Syringe according to claim 1, with a conical insertion region (16) at the upper end of the centering region (11) and/or a conical transition region (10) between the centering region (11) and the cylindrical piston movement area (5) of the syringe cylinder (2).

4. Syringe according to claim 1, in which the centering flange (12) has an external diameter of approximately 21 to 24 mm and/or a height of approximately 3.2 to 4.5 mm and/or the centering region is at a distance of at least 3 to 6 mm from the upper end of the syringe cylinder.

5. Syringe according to claim 1, in which the syringe piston (3) at the top has a disc (24) below the coupling piece (21) and between the disc (24) and the cylindrical centering region an annular gap (290) is present with a gap width of 0.5 to 2.5 mm.

6. Syringe according to claim 1, which has a filling volume selected from the volumes 10 ml, 5 ml, 2.5 ml, 1 ml, 0.5 ml, 0.2 ml, and 0.1 ml.

7. Syringe according to claim 1 in combination with a metering device (370).

8. A syringe in combination with a metering device (370), the syringe being for use with a metering device (370) comprising a centering element (60) with an axial through-passage in a cylindrical receiver (39) at the lower end of a housing for a syringe cylinder (2) and an axially displaceable piston receiver (43) within the housing for a syringe piston (3), comprising
   a syringe cylinder (2)
   and a syringe piston (3),
   the syringe cylinder (2) comprising an outlet at the bottom and a top,
   a centering flange at the top of said syringe cylinder on an external periphery (12) for inserting into the receiver (39) of a metering device (370),
   said syringe cylinder including a cylindrical piston movement area (5) connected to the outlet, with a first internal diameter, in which the syringe piston (3) is sealingly guided, and
   at least at a distance of at least 3 mm from the upper end of the syringe cylinder a centering region (11) designed for insertion therein of a circular hollow cylindrical centering element (60) of said metering device (370), which has a second internal diameter, which exceeds the first internal diameter and is at least 16.2 mm and at most 17.7 mm,
   and the syringe piston (3) at the upper end has a coupling piece (21) for inserting into a piston receiver (43) of the metering device (370);
   wherein the metering device (370) comprises:
   a housing (38) comprising
   at its lower end a cylindrical receiver (39) for the centering flange (12) of the syringe cylinder (2) with an axial opening (40) for axially inserting the centering flange (12) into a fastening position in the receiver (39),
   a centering element (60) arranged in the receiver (39) aligned with the axial opening (40) with an axial through-passage for axially inserting into a cylindrical centering region (11) of a syringe cylinder (2),
   a receiving body (42) with a piston receiver (43) for axially inserting a coupling piece (21) into a fastening position,
   fastening devices (47, 50) for releasably holding the centering flange (12) and coupling piece (21) in their fastening positions in the receiver (39) and in the piston receiver (43),
   the fastening devices (47, 50) comprising radially positionable gripping devices for gripping the centering flange (12) and the coupling piece (21) in the fastening positions and
   piston adjusting devices for displacing the receiving body (42) in the housing (38).

9. A syringe set comprising a plurality of syringes with different filling volumes for use with a metering device (370) comprising a centering element (60) with an axial through-passage in a receiver (39) for a syringe cylinder (2) and an axially displaceable piston receiver (43) for a syringe piston (3),
   each syringe comprising
   a syringe cylinder (2)
   and a syringe piston (3)
   the syringe cylinder (2) at the bottom comprising an outlet and a top,
   at the top of said syringe cylinder on an external periphery a centering flange (12) for inserting into a receiver (39) of a metering device (370),
   said syringe cylinder including a cylindrical piston movement area (5) connected to the outlet, with a first internal diameter, in which the syringe piston (3) is sealingly guided, and
   at least at a distance of at least 3 mm from the upper end of the syringe cylinder a centering region (11) for inserting a centering element of the metering device (370),
   the syringe piston (3) at the upper end comprises a coupling piece (21) for inserting into a piston receiver (43) of the metering device (370), and the centering regions (11) of the syringes (1) with different filling volumes have a matching contour on the inside.

10. The syringe set according to claim 9, in which the external diameter of the centering flange (12) and/or the heights of the centering flange (12) and/or the heights of the centering regions (11) are the same as syringes (1) of different filling volumes.

11. Metering device for use with a syringe (1) comprising a syringe cylinder (2) and a syringe piston (3), the syringe cylinder (2) comprising an outlet at the bottom, a centering flange (12) at the top on an external periphery, a piston movement area (5) connected to the outlet, in which the syringe piston (3) is sealingly guided, and further above a centering region (11) and a coupling piece (21) at the upper end of the syringe piston (3) or for use with a syringe family comprising a plurality of such syringes, having a housing (38) comprising
at its lower end a cylindrical receiver (39) for the centering flange (12) of the syringe cylinder (2) with an axial opening (40) for axially inserting the centering flange (12) into a fastening position in the receiver (39),
a centering element (60) arranged in the receiver (39) aligned with the axial opening (40) with an axial through-passage for axially inserting into a cylindrical centering region (11) of a syringe cylinder (29),
a receiving body (42) with a piston receiver (43) for axially inserting a coupling piece (21) into a fastening position,
fastening devices (47, 50) for releasably holding the centering flange (12) and coupling piece (21) in their fastening positions in the receiver (39) and in the piston receiver (43),
the fastening devices (47, 50) comprising radially positionable gripping devices for gripping the centering flange (12) and the coupling piece (21) in the fastening positions and
piston adjusting devices for displacing the receiving body (42) in the housing (38).

12. Metering device according to claim 11, in which the centering element (60) in a contact region for contact with a centering region of a syringe cylinder (2) has an external diameter of 16.2 to 17.7 mm and/or a wall thickness of 0.4 to 2.5 mm and/or projects relative to a stop for the upper face of the centering flange (12) by 2.2 to 6 mm.

13. Metering device according to claim 11, in which the centering element (60) is arranged rigidly relative to the receiver (39) or resiliently relative to the receiver (39) in the axial direction.

* * * * *